(12) United States Patent
Bhavaraju et al.

(10) Patent No.: US 11,193,924 B2
(45) Date of Patent: *Dec. 7, 2021

(54) END OF LIFE DETECTION FOR ANALYTE SENSORS

(71) Applicant: DexCom, Inc., San Diego, CA (US)

(72) Inventors: Naresh C. Bhavaraju, San Diego, CA (US); Arturo Garcia, Chula Vista, CA (US); Hari Hampapuram, Carlsbad, CA (US); Apurv Ullas Kamath, San Diego, CA (US); Aarthi Mahalingam, San Diego, CA (US); Dmytro Sokolovskyy, San Diego, CA (US); Stephen J. Vanslyke, Carlsbad, CA (US)

(73) Assignee: DexCom, Inc., San Diego, CA (US)

(*) Notice: Subject to any disclaimer, the term of this patent is extended or adjusted under 35 U.S.C. 154(b) by 55 days.

This patent is subject to a terminal disclaimer.

(21) Appl. No.: 16/698,498

(22) Filed: Nov. 27, 2019

(65) Prior Publication Data

US 2020/0096495 A1 Mar. 26, 2020

Related U.S. Application Data

(63) Continuation of application No. 15/195,613, filed on Jun. 28, 2016, now abandoned, which is a
(Continued)

(51) Int. Cl.
*G01N 33/487* (2006.01)
*G16C 20/80* (2019.01)
(Continued)

(52) U.S. Cl.
CPC ..... *G01N 33/48792* (2013.01); *A61B 5/1495* (2013.01); *A61B 5/14532* (2013.01);
(Continued)

(58) Field of Classification Search
CPC .... A61B 2560/0223; A61B 2560/0266; A61B 2560/0276; A61B 2560/028; A61B 5/722; A61B 5/7221
See application file for complete search history.

(56) References Cited

U.S. PATENT DOCUMENTS 4,365,359 A * 12/1982 Raab ............... A61F 2/30767
427/2.26
4,757,022 A 7/1988 Shults et al.
(Continued)

FOREIGN PATENT DOCUMENTS

WO WO 2000/074753 12/2000
WO WO 2007/102842 9/2007
(Continued)

OTHER PUBLICATIONS

Extended European Search Report for Application No. 18168860.7 dated Jul. 13, 2018, 8 pages.
(Continued)

*Primary Examiner* — Michael J Dalbo
(74) *Attorney, Agent, or Firm* — Knobbe Martens Olson & Bear, LLP

(57) ABSTRACT

Systems and methods for processing sensor data and end of life detection are provided. In some embodiments, a method for determining the end of life of a continuous analyte sensor includes evaluating a plurality of risk factors using an end of life function to determine an end of life status of the sensor and providing an output related to the end of life status of the sensor. The plurality of risk factors may be selected from the list including the number of days the sensor has been in use, whether there has been a decrease in signal sensitivity, whether there is a predetermined noise pattern, whether there is a predetermined oxygen concentration pattern, and error between reference BG values and EGV sensor values.

28 Claims, 20 Drawing Sheets

Related U.S. Application Data continuation of application No. 14/523,323, filed on Oct. 24, 2014, now Pat. No. 9,585,609, which is a continuation of application No. 13/733,742, filed on Jan. 3, 2013, now Pat. No. 9,211,092.

(51) Int. Cl.

| | |
|---|---|
| *G16C 99/00* | (2019.01) |
| *A61B 5/00* | (2006.01) |
| *G01M 99/00* | (2011.01) |
| *A61B 5/145* | (2006.01) |
| *A61B 5/1495* | (2006.01) |
| *G01N 33/49* | (2006.01) |
| *G01N 33/66* | (2006.01) |

(52) U.S. Cl.
CPC ......... *A61B 5/7221* (2013.01); *G01M 99/008* (2013.01); *G01N 33/49* (2013.01); *G01N 33/66* (2013.01); *G16C 20/80* (2019.02); *G16C 99/00* (2019.02); *A61B 2560/028* (2013.01); *A61B 2560/0223* (2013.01); *A61B 2560/0266* (2013.01); *A61B 2560/0276* (2013.01)

(56) References Cited

U.S. PATENT DOCUMENTS

| | | | |
|---|---|---|---|
| 4,787,398 A | 11/1988 | Garcia et al. | |
| 5,448,835 A * | 9/1995 | Lewis | G01C 17/26 33/355 R |
| 5,497,772 A | 3/1996 | Schulman et al. | |
| 6,050,962 A * | 4/2000 | Kramer | A61B 5/1071 600/595 |
| 6,248,067 B1 | 6/2001 | Causey et al. | |
| 6,546,269 B1 | 4/2003 | Kurnik | |
| 6,558,351 B1 | 5/2003 | Steil et al. | |
| 6,701,274 B1 | 3/2004 | Eryurek et al. | |
| 6,741,919 B1 * | 5/2004 | Schuster | G05B 9/02 701/29.4 |
| 6,996,374 B1 | 2/2006 | Bao et al. | |
| 8,103,456 B2 | 1/2012 | Doniger et al. | |
| 8,135,548 B2 | 3/2012 | Breton et al. | |
| 8,260,393 B2 | 9/2012 | Kamath et al. | |
| 8,265,725 B2 | 9/2012 | Brauker et al. | |
| 8,306,766 B2 | 11/2012 | Mueller et al. | |
| 8,473,220 B2 | 6/2013 | Doniger et al. | |
| 8,484,005 B2 | 7/2013 | Hayter et al. | |
| 8,868,151 B2 | 10/2014 | Telson et al. | |
| 9,211,092 B2 * | 12/2015 | Bhavaraju | A61B 5/14532 |
| 9,215,995 B2 | 12/2015 | Gottlieb et al. | |
| 9,474,478 B2 * | 10/2016 | Bhavaraju | A61B 5/7221 |
| 9,585,609 B2 | 3/2017 | Bhavaraju et al. | |
| 9,977,010 B2 | 5/2018 | Bhavaraju et al. | |
| 2006/0036145 A1 | 2/2006 | Brister et al. | |
| 2006/0142651 A1 | 6/2006 | Brister et al. | |
| 2007/0203966 A1 | 8/2007 | Brauker et al. | |
| 2008/0167543 A1 | 7/2008 | Say et al. | |
| 2008/0172205 A1 | 7/2008 | Breton et al. | |
| 2009/0043525 A1 | 2/2009 | Brauker et al. | |
| 2009/0055149 A1 | 2/2009 | Hayter et al. | |
| 2009/0069213 A1 | 3/2009 | Avila et al. | |
| 2009/0156924 A1 | 6/2009 | Shariati et al. | |
| 2009/0178459 A1 * | 7/2009 | Li | A61B 5/155 73/1.02 |
| 2009/0192366 A1 | 7/2009 | Mensinger et al. | |
| 2009/0247856 A1 | 10/2009 | Boock et al. | |
| 2010/0030485 A1 | 2/2010 | Brauker et al. | |
| 2010/0179402 A1 | 7/2010 | Goode et al. | |
| 2010/0179408 A1 | 7/2010 | Kamath et al. | |
| 2010/0185065 A1 | 7/2010 | Goode et al. | |
| 2010/0191472 A1 | 7/2010 | Doniger et al. | |
| 2010/0270180 A1 | 10/2010 | Liu et al. | |
| 2011/0024307 A1 * | 2/2011 | Simpson | A61B 5/14517 205/782 |
| 2011/0027127 A1 | 2/2011 | Simpson et al. | |
| 2011/0029269 A1 | 2/2011 | Hayter et al. | |
| 2011/0184267 A1 * | 7/2011 | Duke | A61B 5/725 600/365 |
| 2011/0201911 A1 | 8/2011 | Johnson et al. | |
| 2011/0218414 A1 | 9/2011 | Kamath et al. | |
| 2011/0224523 A1 | 9/2011 | Budiman | |
| 2011/0319734 A1 | 12/2011 | Gottlieb et al. | |
| 2012/0078071 A1 * | 3/2012 | Bohm | A61B 5/14532 600/345 |
| 2012/0108931 A1 | 5/2012 | Taub et al. | |
| 2012/0123691 A1 | 5/2012 | Doniger et al. | |
| 2012/0173200 A1 | 7/2012 | Breton et al. | |
| 2012/0197222 A1 | 8/2012 | Donnay et al. | |
| 2012/0262298 A1 | 10/2012 | Böhm et al. | |
| 2012/0265035 A1 | 10/2012 | Böhm et al. | |
| 2012/0296189 A1 | 11/2012 | Bhogal et al. | |
| 2013/0046483 A1 | 2/2013 | Mansouri et al. | |
| 2014/0188402 A1 | 7/2014 | Garcia et al. | |
| 2016/0183858 A1 | 6/2016 | Bhavaraju et al. | |
| 2016/0302701 A1 | 10/2016 | Bhavaraju et al. | |

FOREIGN PATENT DOCUMENTS

| | | |
|---|---|---|
| WO | WO 2008/052199 | 5/2008 |
| WO | WO 2010/088568 | 8/2010 |

OTHER PUBLICATIONS

International Preliminary Report on Patentability for Application No. PCT/US2013/074321 dated Jul. 16, 2015, 9 pages.
International Search Report and Written Opinion for Application No. PCT/US2013/074321 dated Jun. 12, 2014, 12 pages.
Alfons et al., "Sparse Least Trimmed Squares Regression", imsart-aoas ver. May 20, 2011 file: sparseLTS.tex date: Nov. 21, 2011 (Submitted to the Annals of Applied Statistics); 20 pages.
Frei et al., "Least Squares Acceleration Filtering for the Estimation of Signal Derivatives and Sharpness at Extema", IEEE Transactions on Biomedical Engineering vol. 46(8):971-977.
Frei et al., "Intrinsic time-scale decomposition: time-frequency-energy analysis and real-time filtering of non-stationary signals", Proc R Soc A: Mathematical, Physical and Engineering Sciences A 2007, 463:321-342 (published online Aug. 15, 2006).
Murray et al., [Eds.], "Molecular Electrostatic Potentials—Concepts and Applications" in Theoretical and Computational Chemistry; Elsevier 1996; p. 148.
Pierna et al., "Methods for outlier detection in prediction", Chemomet Intel Lab Sys. (2002) 63:27-39.
Pison et al., "Small Sample Corrections for LTS and MCD", Metrika (Apr. 2002) 55(1-2):111-123.
Rousseeuw P.J., "Least Median of Squares Regression", J Am Statist Assoc. (1984) 76(288):871-880.
Rousseeuw et al., "Recent Developments in PROGRESS", IMS Lecture Notes a the University of Antwerp, Belgium, (1997) vol. 31 in 16 pages.
Rousseeuw et al., "Computing LTS Regression for Large Data Sets", Technical Report at the University of Antwerp, Belgium (1999) in 21 pages.
Wikipedia, the free encyclopedia, "Spectral density", downloaded from http://en.wikipedia.org/wiki/Spectral_density Jan. 29, 2013 in 8 pages.
Zong et al., "Reduction of false arterial blood pressure alarms using signal quality assessment and relationships between the electrocardiogram and arterial blood pressure", Med Biol Eng Comput. (2004) 42(5):698-706.
Extended European Search Report for Application No. 20189907.7, dated Dec. 10, 2020, 9 pages.

* cited by examiner

END OF LIFE DETECTION FOR ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/195,613, filed Jun. 28, 2016, which is a continuation of U.S. application Ser. No. 14/523,323, filed Oct. 24, 2014, now U.S. Pat. No. 9,585,609, which is a continuation of U.S. application Ser. No. 13/733,742, filed Jan. 3, 2013, now U.S. Pat. No. 9,211,092. The aforementioned applications are incorporated by reference herein in their entirety, and are hereby expressly made a part of this specification.

TECHNICAL FIELD

The embodiments described herein relate generally to systems and methods for processing sensor data from continuous analyte sensors and for detection of end of life of the sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

One of the major perceived benefits of a continuous analyte sensor is the ability of these devices to be used continuously for a number of days, e.g., 1, 3, 5, 6, 7, 9, 10, 14 days or more. While these various devices may have been approved for a certain number of days, and sometimes are used "off label" beyond their approved number of days, the performance of the sensors are known to degrade over the lifetime. And, because no environment is the same for any two sensors, the lifetime of any particular sensor may in actuality be less than the approved lifetime of the sensor. Consequently, it would be beneficial to know the status or time for which the end of life of a sensor is near, so that the user may be informed that the sensor should be changed.

SUMMARY

The present systems and methods relate to processing analyte sensor data. The systems and methods enable intelligence in the determination of performance issues related to reference data being entered into the sensor and the sensor itself, in response to which, appropriate action may be taken by the system or prompted to be taken by the user.

In a first aspect, a method is provided for determining an end of life of a continuous analyte sensor, comprising: evaluating a plurality of risk factors associated with end of life symptoms of a sensor; determining an end of life status of the sensor based on the evaluation of the plurality of risk factors; and providing an output related to the end of life status of the sensor, wherein the plurality of risk factors comprise at least two risk factors selected from the group consisting of a number of days the sensor has been in use, a rate of change of sensor sensitivity, end of life noise, oxygen concentration, glucose patterns, error between reference values, and sensor values in clinical units.

In an embodiment of the first aspect, one of the at least two risk factors comprises a number of days the sensor has been in use, and wherein evaluating a number of days the sensor has been in use comprises at least one of evaluating an amount of time since the sensor has been initialized, evaluating an amount of time since the sensor has been implanted, or evaluating an amount of time since the sensor has been initially calibrated.

In an embodiment of the first aspect, one of the at least two risk factors comprises a rate of change of sensor sensitivity, and wherein evaluating a rate of change of sensor sensitivity comprises evaluating at least one of a direction of rate of change of sensor sensitivity, an amplitude of rate of change of sensor sensitivity, a derivative of rate of change of sensor sensitivity or a comparison of the rate of change of sensor sensitivity to a priori rate of change sensitivity information.

In an embodiment of the first aspect, one of the at least two risk factors comprises end of life noise, and wherein evaluating end of life noise comprises evaluating at least one of duration of noise, a magnitude of noise, a history of noise, a spectral content of a signal from the sensor, spikes in the signal from the sensor, skewness of the signal of the sensor or noise patterns by pattern recognition algorithms.

In an embodiment of the first aspect, one of the at least two risk factors comprises end of life noise, and wherein evaluating end of life noise comprises evaluating at least two of duration of noise, a magnitude of noise, a history of noise, a spectral content of a signal from the sensor, spikes in the signal from the sensor, skewness of the signal of the sensor or noise patterns by pattern recognition algorithms.

In an embodiment of the first aspect, one of the at least two risk factors comprises glucose patterns, and wherein evaluating glucose patterns comprises evaluating at least one of mean glucose, glucose variability, peak-to-peak glucose excursions, or expected versus unexpected glucose trends based on timing.

In an embodiment of the first aspect, one of the at least two risk factors comprises error between reference values and sensor values in clinical units, and wherein evaluating error between reference values and sensor values in clinical units comprises evaluating at least one of a direction of error between reference values and sensor values in clinical units, a linearity of the sensor, or an error at calibration.

In an embodiment of the first aspect, the evaluating a plurality of risk factors comprises translating outputs of the plurality of risk factor evaluations to end of life risk factor values.

In an embodiment of the first aspect, translating an output of end of life risk factor values comprises determining a likelihood of recovery.

In an embodiment of the first aspect, the determining an end of life status comprises combining the end of life risk factor values into a combined end of life score.

In an embodiment of the first aspect, the determining an end of life status is based on the combined end of life score.

In an embodiment of the first aspect, combining the end of life risk factor values into a combined end of life score comprises weighting one or more of the plurality of risk factors.

In an embodiment of the first aspect, each of the plurality of risk factors is partially indicative of the end of life of the sensor based on a comparison of the risk factor to one or more criteria.

In an embodiment of the first aspect, if at least two of the plurality of risk factors are determined to meet the one or more criteria, respectively, then the combination of the at least two variables is indicative of the end of life of the sensor.

In an embodiment of the first aspect, determining the end of life status comprises using a probability analysis, a decision fusion, linear discriminant analysis or fuzzy logic.

In an embodiment of the first aspect, the output related to the end of life status is displayed on a user interface.

In an embodiment of the first aspect, the output related to the end of life status comprises instructions to change the sensor.

In an embodiment of the first aspect, the output related to the end of life status comprises a data transmission.

In an embodiment of the first aspect, the method is implemented on a computer having a processor and a memory coupled to said processor, wherein at least one of the evaluating, the determining, and the providing is performed using the processor.

In a second aspect, a system is provided for determining an end of life of a continuous analyte sensor, the system comprising sensor electronics configured to be operably connected to a continuous analyte sensor, the sensor electronics configured to: evaluate a plurality of risk factors associated with end of life symptoms of a sensor; determine an end of life status of the sensor based on the evaluation of the plurality of risk factors; and provide an output related to the end of life status of the sensor, wherein the plurality of risk factors comprise at least two risk factors selected from the group consisting of a number of days the sensor has been in use, a rate of change of sensor sensitivity, end of life noise, oxygen concentration, glucose patterns, error between reference values and sensor values in clinical units.

In an embodiment of the second aspect, one of the at least two risk factors comprises a number of days the sensor has been in use, and wherein the sensor electronics are configured to evaluate a number of days the sensor has been in use by at least one of evaluating an amount of time since the sensor has been initialized, evaluating an amount of time since the sensor has been implanted, or evaluating an amount of time since the sensor has been initially calibrated.

In an embodiment of the second aspect, one of the at least two risk factors comprises a rate of change of sensor sensitivity, and wherein the sensor electronics are configured to evaluate a rate of change of sensor sensitivity by evaluating at least one of a direction of rate of change of sensor sensitivity, an amplitude of rate of change of sensor sensitivity, a derivative of rate of change of sensor sensitivity, or a comparison of the rate of change of sensor sensitivity to a priori rate of change sensitivity information.

In an embodiment of the second aspect, one of the at least two risk factors comprises end of life noise, and wherein the sensor electronics are configured to evaluate end of life noise by evaluating at least one of duration of noise, a magnitude of noise, a history of noise, a spectral content of a signal from the sensor, spikes in the signal from the sensor, skewness of the signal of the sensor, or noise patterns by pattern recognition algorithms.

In an embodiment of the second aspect, one of the at least two risk factors comprises end of life noise, and wherein the sensor electronics are configured to evaluate end of life noise by evaluating at least two of duration of noise, a magnitude of noise, a history of noise, a spectral content of a signal from the sensor, spikes in the signal from the sensor, skewness of the signal of the sensor, or noise patterns by pattern recognition algorithms.

In an embodiment of the second aspect, one of the at least two risk factors comprises glucose patterns, and wherein the sensor electronics are configured to evaluate glucose patterns by evaluating at least one of mean glucose, glucose variability, peak-to-peak glucose excursions, or expected versus unexpected glucose trends based on timing.

In an embodiment of the second aspect, one of the at least two risk factors comprises error between reference values and sensor values in clinical units, and wherein the sensor electronics are configured to evaluate error between reference values and sensor values in clinical units by evaluating at least one of a direction of error between reference values and sensor values in clinical units, or a linearity of the sensor and an error at calibration.

In an embodiment of the second aspect, the sensor electronics are configured to evaluate a plurality of risk factors by translating outputs of the plurality of risk factor evaluations to end of life risk factor values.

In an embodiment of the second aspect, the sensor electronics are configured to translate an output of end of life risk factor values by determining a likelihood of recovery.

In an embodiment of the second aspect, the sensor electronics are configured to determine an end of life status by combining the end of life risk factor values into a combined end of life score.

In an embodiment of the second aspect, the sensor electronics are configured to determine an end of life status based on the combined end of life score.

In an embodiment of the second aspect, the sensor electronics are configured to combine the end of life risk factor values into a combined end of life score by weighting one or more of the plurality of risk factors.

In an embodiment of the second aspect, each of the plurality of risk factors is partially indicative of the end of life of the sensor based on a comparison of the risk factor to one or more criteria.

In an embodiment of the second aspect, if at least two of the plurality of risk factors are determined to meet the one or more criteria, respectively, then a combination of the at least two variables is indicative of the end of life of the sensor.

In an embodiment of the second aspect, the sensor electronics are configured to determine the end of life status by using a probability analysis, a decision fusion, linear discriminant analysis, or fuzzy logic.

In an embodiment of the second aspect, the output related to the end of life status is displayed on a user interface.

In an embodiment of the second aspect, the output related to the end of life status comprises instructions to change the sensor.

In an embodiment of the second aspect, the output related to the end of life status comprises a data transmission.

In an embodiment of the second aspect, the sensor electronics comprise a processor module, the processor module comprising instructions stored in computer memory, wherein the instructions, when executed by the processor module, cause the sensor electronics to perform the evaluating, the determining and the providing.

In a third aspect, a method is provided for determining if a continuous analyte sensor has been reused, comprising: evaluating a plurality of risk factors associated with end of life symptoms of a sensor; determining an end of life status of the sensor by performing an end of life function based on the evaluation of the plurality of risk factors; and providing an output related to a sensor reuse within a predetermined time frame after sensor initialization if the end of life status meets one or more predetermined sensor reuse criteria, wherein the plurality of risk factors comprise at least two risk factors selected from the group consisting of a number of days the sensor has been in use, a rate of change of sensor sensitivity, end of life noise, oxygen concentration, glucose patterns, error between reference values, and sensor values in clinical units.

In an embodiment of the third aspect, the providing an output comprises disabling display of sensor data responsive to the end of life status meeting the one or more predetermined sensor reuse criteria.

In a fourth aspect, a system is provided for determining if a continuous analyte sensor has been reused, the system comprising sensor electronics configured to be operably connected to a continuous analyte sensor, the sensor electronics configured to: evaluate a plurality of risk factors associated with end of life symptoms of the sensor; determine an end of life status of the sensor by performing an end of life function based on the evaluation of the plurality of risk factors; and provide an output related to the sensor reuse of the sensor within a predetermined time frame after sensor initialization if the end of life status meets one or more predetermined sensor reuse criteria, wherein the plurality of risk factors comprise at least two risk factors selected from the group consisting of a number of days the sensor has been in use, a rate of change of sensor sensitivity, end of life noise, oxygen concentration, glucose patterns, error between reference values, and sensor values in clinical units.

In an embodiment of the fourth aspect, the providing an output comprises disabling display of sensor data responsive to the end of life status meeting the one or more predetermined sensor reuse criteria.

In an embodiment of the fourth aspect, the sensor electronics comprise a processor module, the processor module comprising instructions stored in computer memory, wherein the instructions, when executed by the processor module, cause the sensor electronics to perform the evaluating and the providing.

In a fifth aspect, a method is provided for detecting outliers in analyte sensor data, comprising: iteratively evaluating a plurality of subsets of a calibration data set to determine a best subset; identifying a boundary or confidence interval associated with the best subset; identifying values outside the boundary or confidence interval as possible outliers; evaluating the relevancy of the possible outliers to determine outlier information; and processing responsive to the outlier information.

In an embodiment of the fifth aspect, the evaluation of subsets to determine a best subset includes generating a regression line or a convex hull.

In an embodiment of the fifth aspect, the regression line is generated using at least ½ of data points in the calibration set.

In an embodiment of the fifth aspect, the evaluating the relevancy of the possible outliers to determine outlier information comprises at least one of evaluating the clinical relevancy of the possible outliers, discrimination of the root cause of the error in the possible outliers, and trends of the outlier information.

In an embodiment of the fifth aspect, the evaluating the relevancy comprises examining one or more factors from the following list: the amplitude of error of a data point relative to the best line, the direction of error a data point relative to the best line, a clinical risk of the data at a time stamp of the data point, a rate of change of the analyte concentration or derivative of the sensor data associated with a data point, a rate of acceleration or deceleration of the analyte concentration or second derivative of the sensor data associated with the data point.

In an embodiment of the fifth aspect, the processing responsive to the outlier information comprises removing the outlier temporarily or permanently from the calibration set, prospectively or retrospectively.

In an embodiment of the fifth aspect, the processing responsive to the outlier information comprises flagging an outlier and keeping the outlier in the calibration data set until the next data point is collected.

In a sixth aspect, a system is provided for detecting outliers in analyte sensor data, the system comprising sensor electronics configured to be operably connected to a continuous analyte sensor, the sensor electronics configured to: iteratively evaluate a plurality of subsets of a calibration data set to determine a best subset; identify a boundary or confidence interval associated with a best subset; identify values outside the boundary or confidence interval as possible outliers; evaluate the relevancy of the possible outliers to determine outlier information; and process responsive to the outlier information.

In an embodiment of the sixth aspect, the evaluation of subsets to determine a best subset includes generating a regression line or a convex hull.

In an embodiment of the sixth aspect, the regression line is generated using at least ½ of data points in the calibration set.

In an embodiment of the sixth aspect, the evaluating the relevancy of the possible outliers to determine outlier information comprises at least one of evaluating the clinical relevancy of the possible outliers, discrimination of the root cause of the error in the possible outlier, and trends of outlier information.

In an embodiment of the sixth aspect, the evaluating the relevancy comprises examining one or more factors from the following list: the amplitude of error of a data point relative to the best line, the direction of error a data point relative to the best line, a clinical risk of the data at a time stamp of the data point, a rate of change of the analyte concentration or derivative of the sensor data associated with a data point, a rate of acceleration or deceleration of the analyte concentration or second derivative of the sensor data associated with the data point.

In an embodiment of the sixth aspect, the processing comprises removing the outlier temporarily or permanently from the calibration set, prospectively or retrospectively.

In an embodiment of the sixth aspect, the processing comprises flagging an outlier and keeping the outlier in the calibration data set until the next data point is collected.

In an embodiment of the sixth aspect, the sensor electronics comprise a processor module, the processor module comprising instructions stored in computer memory, wherein the instructions, when executed by the processor module, cause the sensor electronics to perform the evaluating and the processing.

In a seventh aspect, a method is provided for detecting outliers in analyte sensor data, comprising: iteratively evaluating a plurality of subsets of a calibration data set; identifying a possible outlier based on one or more first outlier criteria; evaluating the relevancy of the possible outlier based on one or more relevancy criteria to discriminate a root case of the possible outlier; and processing outlier information responsive thereto.

In an embodiment of the seventh aspect, the evaluating the relevancy comprises evaluating at least one of: time since sensor implant, trends in outlier evaluation, the amplitude of error of a data point relative to the best line, the direction of error a data point relative to the best line, a clinical risk of the data at a time stamp of the data point, a rate of change of the analyte concentration or derivative of the sensor data associated with a data point, a rate of acceleration or deceleration of the analyte concentration or second derivative of the sensor data associated with the data point.

In an eighth aspect, a system is provided for detecting outliers in analyte sensor data, the system comprising sensor electronics configured to be operably connected to a continuous analyte sensor, the sensor electronics configured to: iteratively evaluate a plurality of subsets of a calibration data set; identify a possible outlier based on one or more first outlier criteria; evaluate the relevancy of the possible outlier based on one or more relevancy criteria to discriminate a root case of the possible outlier; and process outlier information responsive thereto.

In an embodiment of the eighth aspect, the evaluating the relevancy comprises evaluating at least one of: time since sensor implant, trends in outlier evaluation, the amplitude of error of a data point relative to the best line, the direction of error a data point relative to the best line, a clinical risk of the data at a time stamp of the data point, a rate of change of the analyte concentration or derivative of the sensor data associated with a data point, a rate of acceleration or deceleration of the analyte concentration or second derivative of the sensor data associated with the data point.

In an embodiment of the eighth aspect, the sensor electronics comprise a processor module, the processor module comprising instructions stored in computer memory, wherein the instructions, when executed by the processor module, cause the sensor electronics to perform the evaluating and the processing.

BRIEF DESCRIPTION OF THE DRAWINGS

The details of the present disclosure, both as to its structure and operation, may be understood in part by study of the accompanying drawings, in which like reference numerals refer to like parts. The drawings are not necessarily to scale, emphasis instead being placed upon illustrating the principles of the disclosure.

DETAILED DESCRIPTION

Definitions

Figure 1A:
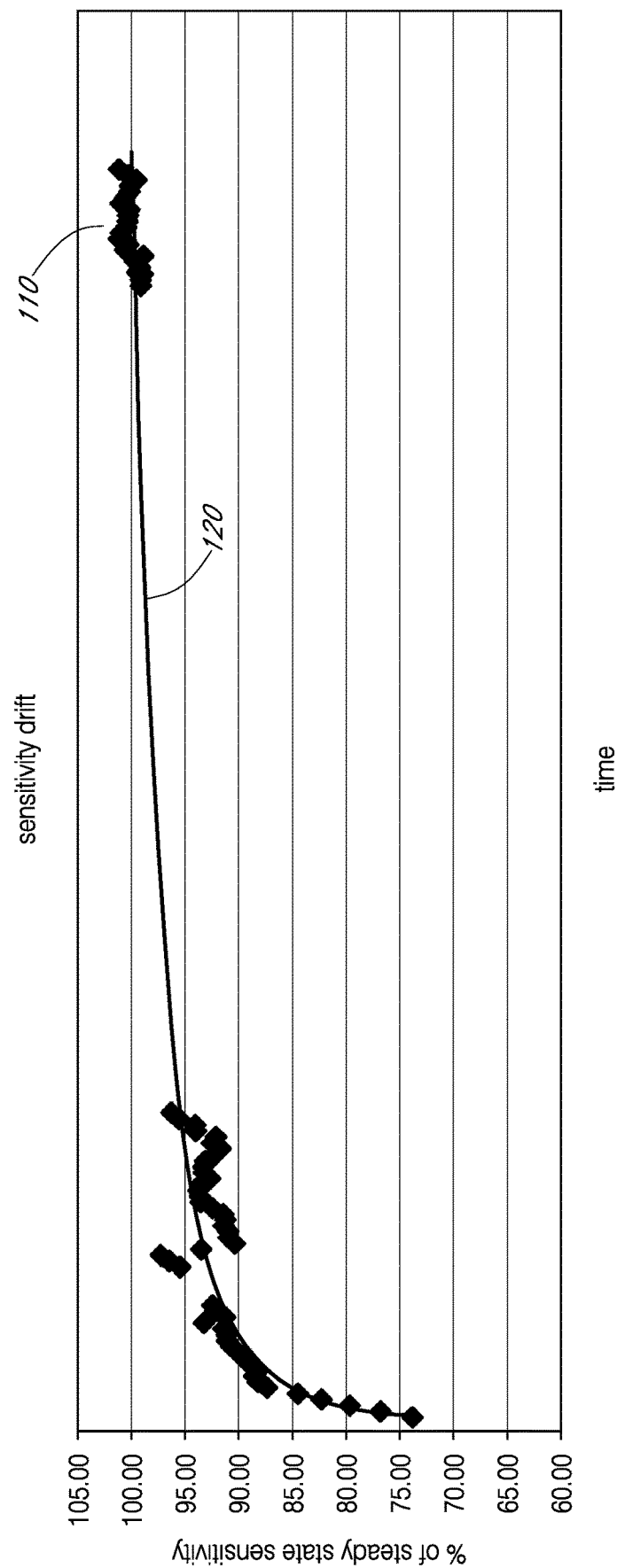
FIG. 1A illustrates a schematic diagram of sensor sensitivity as a function of time during a sensor session, in accordance with an embodiment.

In order to facilitate an understanding of the embodiments described herein, a number of terms are defined below.

The term "analyte," as used herein, is a broad term, and is to be given its ordinary and customary meaning to a person of ordinary skill in the art (and is are not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (e.g., by continuously or continually adjusting or determining the sensor's sensitivity and background), for example, at time intervals ranging from fractions of a second up to, for example, 1, 2, or 5 minutes, or longer.

The terms "raw data stream" and "data stream," as used herein, are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced matched data pairs from a substantially continuous analyte sensor, which comprises individual measurements taken at time intervals ranging from fractions of a second up to, for example, 1, 2, or 5 minutes or longer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "matched data pair" or "data pair" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "calibration" as used herein is a broad term, and is to be given its ordinary and customary meaning to a person of ordinary skill in the art (and is not to be limited to a special or customized meaning), and refers without limitation to the process of determining the relationship between raw sensor data (e.g., analog (nA) or digital units (counts) to clinically meaningful units (e.g., mg/dL or mmol/L for glucose)). In some embodiments, the process includes determining the relationship by pairing the sensor data and the corresponding reference data, however other calibration techniques (without pairing sensor data and time-corresponding reference data) may also be used. In some embodiments, namely, in continuous analyte sensors, calibration can be updated or recalibrated over time (e.g., once or twice daily, or more, or when reference data is provided by the host) as changes in the relationship between the sensor data and reference data occur, for example, due to changes in sensitivity, baseline, transport, metabolism, or the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, also referred to as a transformation function, to provide a meaningful value to a user.

The term "calibration set" as used herein is a broad term, and is to be given its ordinary and customary meaning to a person of ordinary skill in the art (and is not to be limited to a special or customized meaning), and refers without limitation to a set of data comprising information useful for calibration. In some embodiments, the calibration set is formed from one or more matched data pairs, which are used to determine the relationship between the reference data and the sensor data; however other data derived pre-implant, externally or internally may also be used.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time Overview Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on some or all of the matched data pairs (e.g., by using least squares regression) to generate a transformation function that defines a relationship between a sensor signal and an estimated glucose concentration.

In critical care settings, calibration of continuous analyte sensors is often performed by using, as reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and input into the continuous analyte sensor system. This calibration procedure typically involves frequent finger stick measurements, which can be inconvenient and painful.

In certain embodiments, the continuous analyte sensor includes one or more working electrodes and one or more reference and/or counter electrodes, which operate together to measure a signal associated with a concentration of the analyte in the host. The output signal from the working electrode is typically a raw data stream that is calibrated, processed, and used to generate an estimated analyte (e.g., glucose) concentration. In certain embodiments, the continuous analyte sensor may measure an additional signal associated with the baseline and/or sensitivity of the sensor, thereby enabling monitoring of baseline and/or additional monitoring of sensitivity changes or drift that may occur in a continuous analyte sensor over time.

In some embodiments, the sensor extends through a housing, which maintains the sensor on the skin and provides for electrical connection of the sensor to sensor electronics. In one embodiment, the sensor is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. Other embodiments of the elongated conductive body are disclosed in U.S. Patent Application Publication No. 2011/0027127, which is incorporated herein by reference in its entirety. Preferably, a membrane system is deposited over at least a portion of electroactive surfaces of the sensor (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferants, and/or hydrophilicity at the electrochemically reactive surfaces of the sensor interface. Disclosures regarding the different membrane systems that may be used with the embodiments described herein are described in U.S. Patent Publication No. US-2009-0247856-A1, which is incorporated herein by reference in its entirety. In addition to wire based sensors, the systems and methods described here may be applicable to other invasive, minimally invasive or non-invasive sensor technologies, such as the planar substrate-based sensor technologies.

Calibrating sensor data from continuous analyte sensors generally involves defining a relationship between sensor-generated measurements (e.g., in units of nA or digital counts after A/D conversion) and clinically relevant values (e.g., in units of mg/dL or mmol/L). In certain embodiments, one or more reference measurements obtained shortly after the analyte sensor is manufactured, and before sensor use, are used for calibration. The reference measurement may be obtained in many forms. For example, in certain embodiments, the reference measurement may be determined from a ratio or correlation between the sensitivity of a sensor (e.g., from a certain sensor lot) with respect to in vivo analyte concentration measurements and the sensitivity of another sensor (e.g., from the same lot made in substantially the same way under substantially same conditions) with respect to in vitro analyte concentration measurements at a certain time period. By providing a continuous analyte sensor with a predetermined in vivo to in vitro ratio and a predetermined sensitivity profile (as described in more detail elsewhere herein), self-calibration of the sensor can be achieved in conjunction with high levels of sensor accuracy.

Determination of Sensor Sensitivity

In certain embodiments, self-calibration of an analyte sensor system can be performed by determining sensor sensitivity based on a sensitivity profile (and a measured or estimated baseline), so that the following equation can be solved:

$$y=mx+b$$

wherein y represents the sensor signal (counts), x represents the estimated glucose concentration (mg/dL), m represents the sensor sensitivity to the analyte (counts/mg/dL), and b represents the baseline signal (counts). From this equation, a transformation function can be formed, whereby a sensor signal is converted into an estimated glucose concentration.

Figure 1B:
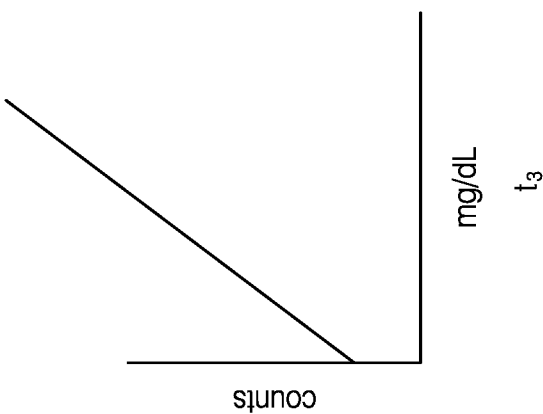
FIG. 1B illustrates schematic representations of sensitivity and baseline derived from a regression at different time periods of a sensor session, in accordance with the embodiment of FIG. 1A.
Figure 1B:
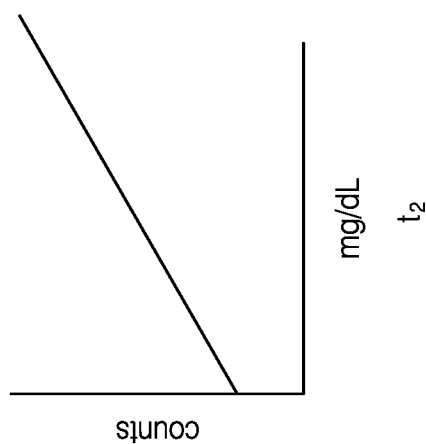
Figure 1B:
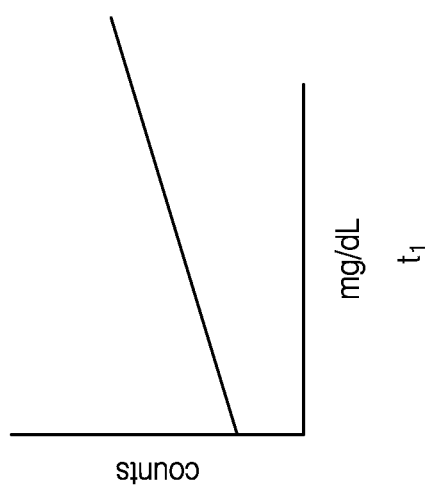

It has been found that a sensor's sensitivity to analyte concentration during a sensor session will often change or drift as a function of time. FIG. 1A illustrates this phenomenon and provides a plot of sensor sensitivities 110 of a group of continuous glucose sensors as a function of time during a sensor session. FIG. 1B provides three plots of transformation functions at three different time periods of a sensor session. As shown in FIG. 1B, the three transformation functions have different slopes, each of which correspond to a different sensor sensitivity. Accordingly, the differences in slopes over time illustrate that changes or drift in sensor sensitivity occur over a sensor session.

Referring back to the study associated with FIG. 1A, the sensors were made in substantially the same way under substantially the same conditions. The sensor sensitivities associated with the y-axis of the plot are expressed as a percentage of a substantially steady state sensitivity that was reached about three days after start of the sensor session. In addition, these sensor sensitivities correspond to measurements obtained from standard reference glucometers (e.g., from Yellow Springs Instruments). As shown in the plot, the sensitivities (expressed as a percentage of a steady state sensitivity) of each sensor, as measured, are very close to sensitivities of other sensors in the group at any given time of the sensor session. While not wishing to be bound by theory, it is believed that the observed upward trend in sensitivity (over time), which is particularly pronounced in the early part of the sensor session, can be attributed to conditioning and hydration of sensing regions of the working electrode. It is also believed that the glucose concentration of the fluid surrounding the continuous glucose sensor during startup of the sensor can also affect the sensitivity drift.

With the sensors tested in this study, the change in sensor sensitivity (expressed as a percentage of a substantially steady state sensitivity), over a time defined by a sensor session, resembled a logarithmic growth curve. It should be understood that other continuous analyte sensors fabricated with different techniques, with different specifications (e.g., different membrane thickness or composition), or under different manufacturing conditions, may exhibit a different sensor sensitivity profile (e.g., one associated with a linear function). Nonetheless, with improved control over operating conditions of the sensor fabrication process, high levels of reproducibility have been achieved, such that sensitivity profiles exhibited by individual sensors of a sensor population (e.g., a sensor lot) are substantially similar and sometimes nearly identical.

It has been discovered that the change or drift in sensitivity over a sensor session is not only substantially consistent among sensors manufactured in substantially the same way under substantially same conditions, but also that modeling can be performed through mathematical functions that can accurately estimate this change or drift. As illustrated in FIG. 1A, an estimative algorithm function 120 can be used to define the relationship between time during the sensor session and sensor sensitivity. The estimative algorithm function may be generated by testing a sample set (comprising one or more sensors) from a sensor lot under in vivo and/or in vitro conditions. Alternatively, the estimative algorithm function may be generated by testing each sensor under in vivo and/or in vitro conditions.

In some embodiments, a sensor may undergo an in vitro sensor sensitivity drift test, in which the sensor is exposed to changing conditions (e.g., step changes of glucose concentrations in a solution), and an in vitro sensitivity profile of the sensor is generated over a certain time period. The time period of the test may substantially match an entire sensor session of a corresponding in vivo sensor, or it may encompass a portion of the sensor session (e.g., the first day, the first two days, or the first three days of the sensor session, etc.). It is contemplated that the above-described test may be performed on each individual sensor, or alternatively on one or more sample sensors of a sensor lot. From this test, an in vitro sensitivity profile may be created, from which an in vivo sensitivity profile may be modeled and/or formed.

From the in vivo or in vitro testing, one or more data sets, each including matched data pairs associating sensitivity with time, may be generated and plotted. A sensitivity profile or curve can then be fitted to the matched data pairs. If the curve fit is determined to be satisfactory (e.g., if the standard deviation of the generated matched data pairs is less a certain threshold), then the sensor sensitivity profile or curve may be judged to have passed a quality control and suitable for release. From there, the sensor sensitivity profile can be transformed into an estimative algorithm function or alternatively into a look-up table. The algorithm function or look-up table can be stored in a computer-readable memory, for example, and accessed by a computer processor.

The estimative algorithm function may be formed by applying curve fitting techniques that regressively fit a curve to matched data pairs by adjusting the function (e.g., by adjusting parameters of the function) until an optimal fit to the available matched data pairs is obtained. Simply put, a "curve" (e.g., a function sometimes referred to as a "model") is fitted and generated that relates one data value to one or more other data values and selecting parameters of the curve such that the curve estimates the relationship between the data values. By way of example, selection of the parameters of the curve may involve selection of coefficients of a polynomial function. In some embodiments, the curve fitting process may involve evaluating how closely the curve determined in the curve fitting process estimates the relationship between the data values, to determine the optimal fit. The term "curve," as used herein, is a broad term, and is to be given its ordinary and customary meaning to a person of ordinary skill in the art (and is not to be limited to a special or customized meaning), and refers to a function or a graph of a function, which can involve a rounded curve or a straight curve, e.g., a line.

The curve may be formed by any of a variety of curve fitting techniques, such as, for example, the linear least squares fitting method, the non-linear least squares fitting method, the Nelder-Mead Simplex method, the Levenberg-Marquardt method, and variations thereof. In addition, the curve may be fitted using any of a variety of functions, including, but not limited to, a linear function (including a constant function), logarithmic function, quadratic function, cubic function, square root function, power function, polynomial function, rational function, exponential function, sinusoidal function, and variations and combinations thereof. For example, in some embodiments, the estimative algorithm comprises a linear function component which is accorded a first weight $w1$, a logarithmic function component which is accorded a second weight $w2$, and an exponential function component which is accorded a third weight $w3$. In further embodiments, the weights associated with each component can vary as a function of time and/or other parameters, but in alternative embodiment, one or more of these weights are constant as a function of time.

In certain embodiments, the estimative algorithm function's correlation (e.g., $R2$ value), which is a measure of the quality of the fit of the curve to the matched data pairs, with respect to data obtained from the sample sensors, may be one metric used to determine whether a function is optimal. In certain embodiments, the estimative algorithm function formed from the curve fitting analysis may be adjusted to account for other parameters, e.g., other parameters that may affect sensor sensitivity or provide additional information about sensor sensitivity. For example, the estimative algorithm function may be adjusted to account for the sensitivity of the sensor to hydrogen peroxide or other chemical species.

Estimative algorithms formed and used to accurately estimate an individual sensor's sensitivity, at any time during a sensor session, can be based on factory calibration and/or based on a single early reference measurement (e.g., using a single point blood glucose monitor). In some embodiments, sensors across a population of continuous analyte sensors manufactured in substantially the same way under substantially same conditions exhibit a substantially fixed in vivo to in vitro sensitivity relationship. For example, in one embodiment, the in vivo sensitivity of a sensor at a certain time after start of sensor use (e.g., at t=about 5, 10, 15, 30, 60, 120, or 180 minutes after sensor use) is consistently equal to a measured in vitro sensitivity of the sensor or of an equivalent sensor. From this relationship, an initial value of in vivo sensitivity can be generated, from which an algorithmic function corresponding to the sensor sensitivity profile can be formed. Put another way, from this initial value (which represents one point in the sensor sensitivity profile), the rest of the entire sensor sensitivity profile can be determined and plotted. The initial value of in vivo sensitivity can be associated with any portion of the sensor sensitivity profile. In certain embodiments, multiple initial values of in vivo sensitivities, which are time-spaced apart, and which correspond to multiple in vitro sensitivities, can be calculated and combined together to generate the sensor sensitivity profile.

Figure 2A:
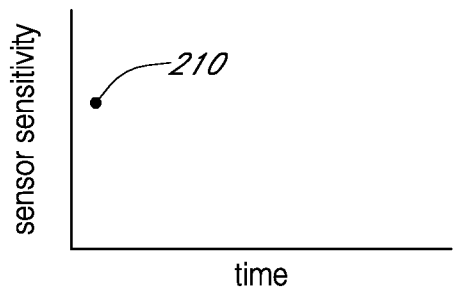
FIGS. 2A-2B and FIGS. 2C-2D collectively illustrate different embodiments of processes for generating a sensor sensitivity profile.
Figure 2B:
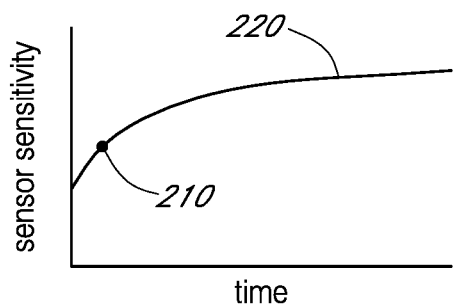
Figure 2C:
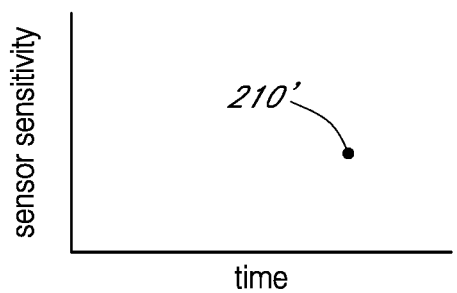
Figure 2D:
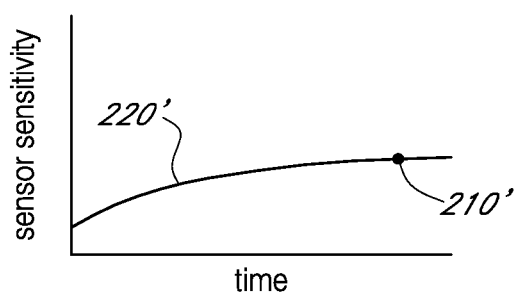

In some embodiments, as illustrated in FIG. 2A, the initial value 210 of in vivo sensitivity is associated with a time corresponding to the start (near the start) of the sensor session. As illustrated in FIG. 2B, based on this initial value 210, the rest of the sensor sensitivity profile 220 is plotted (e.g., plotted forward and backward across the x-axis corresponding to time). However, as illustrated in FIG. 2C, in some embodiments, the initial value 210' may be associated with any other time of the sensor session. For example, as illustrated in FIG. 2C, in one embodiment, the initial value 210' of in vivo sensitivity is associated with a time (e.g., at about day 3) when the sensitivity has substantially reached steady state. From the initial value 210', the rest of the sensor sensitivity profile 220' is plotted, as illustrated in FIG. 2D.

With other embodiments, although the in vivo to in vitro sensitivity relationship was not equal, the relationship nonetheless involved a consistently fixed relationship or function. By having a substantially fixed in vivo to in vitro sensitivity relationship, some of the sensors described herein can be factory calibrated by evaluating the in vitro sensitivity characteristic (e.g., one or more sensitivity values measured at certain time periods) of a sensor from a particular sensor lot at a manufacturing facility, defining the in vivo sensitivity characteristic of other sensors in the same sensor lot based on its relationship with the measured in vitro sensitivity characteristic, and storing this calculated in vivo sensitivity characteristic onto electronics associated with the sensors (e.g., in computer memory of a sensor electronics, discussed more elsewhere herein, configured to be operably coupled to the sensor during sensor use).

Accordingly, with information obtained prior to the sensor session relating to an in vivo to in vitro sensor sensitivity relationship and a predetermined sensor sensitivity profile, factory calibration is achieved in conjunction with high levels of sensor accuracy. For example, in some embodiments, the sensor was capable of achieving an accuracy corresponding to a mean absolute relative difference of no more than about 10% over a sensor session of at least about 3 days, and sometimes at least about 4, 5, 6, 7, or 10 days. In some embodiments, the sensor was capable of achieving an accuracy, over a over a sensor session of at least about 3 days, corresponding to a mean absolute relative difference of no more than about 7%, 5%, or 3%. With factory calibration, the need for recalibration may be eliminated, or else required only in certain circumstances, such as in response to detection of sensor failure.

With reference back to the study associated with FIG. 1A, the sensors were built with a working electrode configured to measure a glucose+baseline signal and a corresponding auxiliary electrode configured to measure only the baseline signal. Sensor electronics in the sensor system subtracted the baseline signal from the glucose+baseline signal to obtain a signal associated entirely or substantially entirely to glucose concentration. In addition, an algorithmic function was generated and stored in sensor electronics associated with the sensors to estimate the sensitivity of these sensors during their lives. This algorithmic function is plotted in FIG. 1A and shown closely overlying the measured sensor sensitivities of the sensors. With the determination of baseline and sensitivity at any given time during the life of a sensor, a transformation function is formed, whereby a sensor signal is converted into an estimated glucose concentration.

While individual sensors of a sensor group manufactured under substantially identical conditions have been found to generally exhibit a substantially similar or a nearly identical sensor sensitivity profile and have a substantially similar or a nearly identical in vivo to in vitro sensor sensitivity relationship, it has been found that at times the actual sensor sensitivity (e.g., sensitivity expressed as an actual sensitivity value, and not as a percentage of a substantially steady state sensitivity) can vary between sensors. For example, even though individual sensors may have been manufactured under substantially identical conditions, they can have different sensitivity characteristics during use if they are exposed to different environment conditions (e.g., exposure to radiation, extreme temperature, abnormal dehydration conditions, or any environment that can damage the enzyme in the sensor membrane or other parts of the sensor, etc.) during the time period between sensor fabrication and sensor use.

Accordingly, to compensate for potential effects resulting from these conditions, in certain embodiments, the continuous analyte sensors are configured to request and accept one or more reference measurements (e.g., from a finger stick glucose measurement or from a calibration solution) at the start of the sensor session. For example, the request for one or more reference measurements can be made at about 15 minutes, 30 minutes, 45 minutes, 1 hour, 2 hours, 3 hours, etc., after activation of the sensor. In some embodiments, sensor electronics are configured to process and use the reference data to generate (or adjust) a sensor sensitivity profile in response to the input of one or more reference measurements into the sensor. For example, if a reference measurement of glucose concentration is taken and input into the sensor at time=x, an algorithmic function of sensor sensitivity can be generated by matching the sensor sensitivity profile at time=x with the reference measurement. Use of the one of the one or more reference measurements at the start of the sensor in conjunction with a predetermined sensor sensitivity profile permits self-calibration of the sensor without or with a reduced need for further reference measurements.

Figure 3:
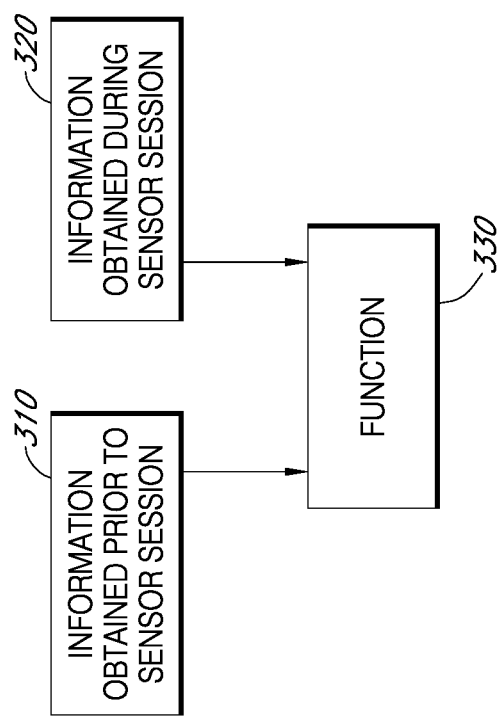
FIG. 3 illustrates a diagram showing different types of information that can be input into the sensor system to define the sensor sensitivity profile over time.

FIG. 3 is a diagram illustrating different types of information that can be input into the sensor system to define the sensor sensitivity profile over time, in one embodiment. Input information can include information obtained prior to the sensor session 310 and information obtained during the sensor session 320. In the embodiment depicted in FIG. 3, both information obtained prior to the sensor session 310 and information obtained during the sensor session 320 are used to generate, adjust, or update a function 330 associated with the sensor sensitivity profile, but in another embodiment, the sensor system may be configured to use only information obtained prior to the sensor session. In certain embodiments, formation of an initial sensor sensitivity profile can occur prior to the sensor session, at the start of the sensor session, or shortly after the start of the sensor session. Additionally, in certain embodiments, the sensor sensitivity profile can be continuously adjusted, regenerated, or updated to account for parameters that may affect sensor sensitivity or provide additional information about sensor sensitivity during the sensor session. Information obtained prior to the sensor session can include, for example, the sensor sensitivity profile that is generated before or at the start of the sensor session, as previously described. It can also include a sensitivity value associated with a substantially fixed in vivo to in vitro sensor sensitivity relationship, as previously described.

Figure 4:
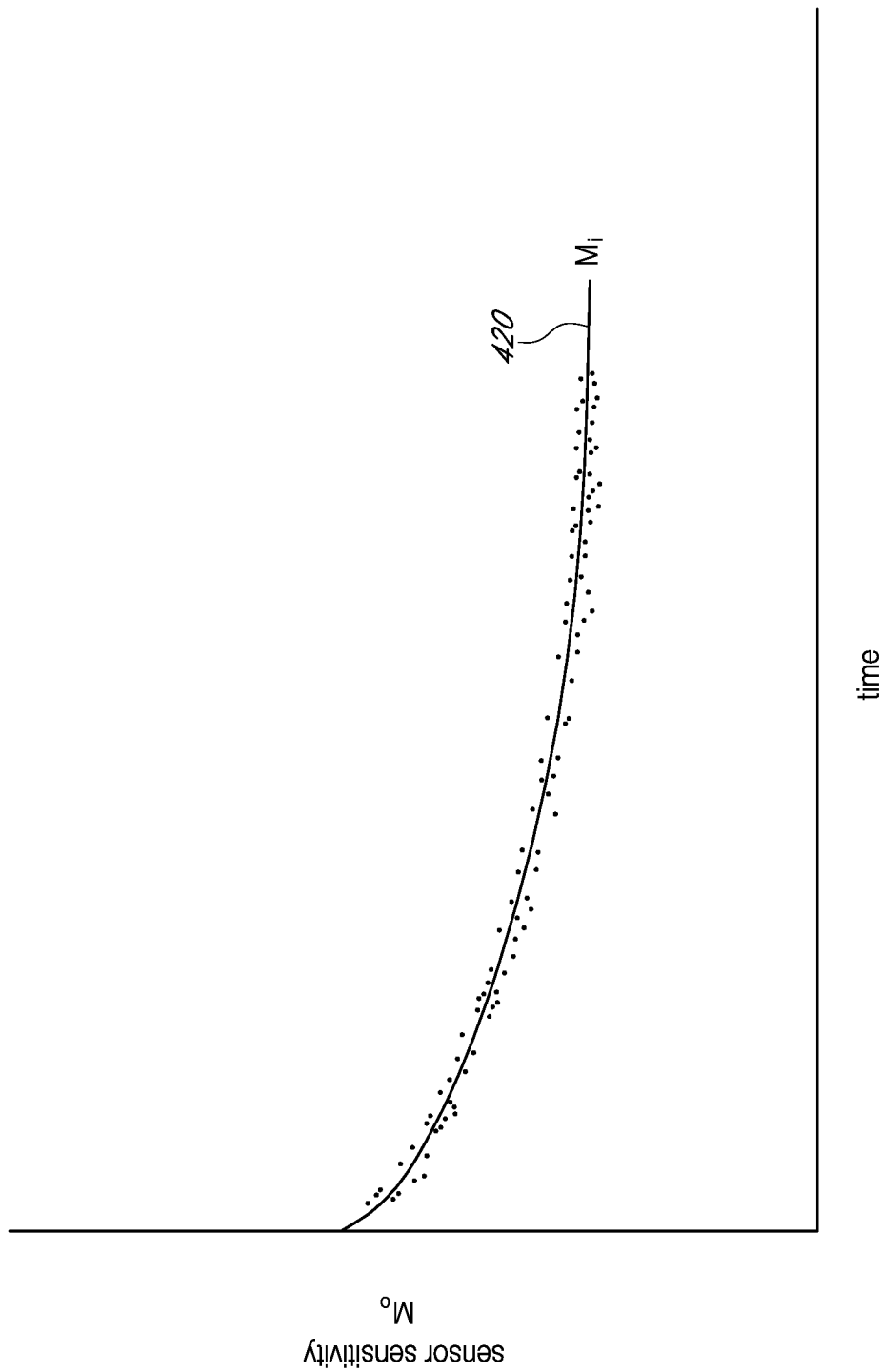
FIG. 4 illustrates a schematic diagram of sensor sensitivity as a function of time between completion of sensor fabrication and the start of the sensor session, in accordance with an embodiment.

Alternatively, instead of a fixed sensitivity value, the in vivo to in vitro sensor sensitivity relationship may be defined as a function of time between completion of sensor fabrication (or the time calibration check was performed on sensors from the same lot) and the start of the sensor session. As shown in FIG. 4, it has been discovered that a sensor's sensitivity to analyte concentration can change as a function of time between completion of sensor fabrication and the start of the sensor session. FIG. 4 illustrates this phenomenon through a plot, which resembles a downward trend in sensitivity over time between completion of sensor fabrication and the start of the sensor session. Similar to the discovered change or drift in sensitivity over time of a sensor session, this change or drift in sensitivity over time between completion of sensor fabrication and the start of the sensor session is generally consistent among sensors that have not only been manufactured in substantially the same way under substantially same conditions, but that also have avoided exposure to certain conditions (e.g., exposure to radiation, extreme temperature, abnormal dehydration conditions, or any environment that can damage the enzyme in the sensor membrane or other parts of the sensor, etc.). Accordingly, the change or drift in sensitivity over time between completion of sensor fabrication and the start of the sensor session can also be modeled through a mathematical function 420 that accurately estimates this change or drift. The estimative algorithm function 420 may be any of a variety of functions, such as, for example, a linear function (including a constant function), logarithmic function, quadratic function, cubic function, square root function, power function, polynomial function, rational function, exponential function, sinusoidal function, and combinations thereof.

Information obtained prior to the sensor session can also include information relating to certain sensor characteristics or properties. By way of example and not to be limiting, information obtained prior to the sensor session may include the particular materials used to fabricate the sensor (e.g., materials used to form the sensor membrane), the thickness of the sensor membrane, the membrane's permeability to glucose or other chemical species, the in vivo or in vitro sensor sensitivity profile of another sensor made in substantially the same way under substantially same conditions, etc. In certain embodiments, information obtained prior to the sensor session can include information relating to the process conditions under which the sensor is fabricated. This information can include, for example, the temperature at which the sensor membrane was cured, the length of time the sensor was dipped in a particular coating solution, etc. In other embodiments, information obtained prior to the sensor session can relate to patient physiological information. For example, the patient's age, body mass index, gender, and/or historic patient sensitivity profiles, can be used as parameters to form the sensor sensitivity profile. Other information obtained prior to the sensor session that may also be used includes information relating to sensor insertion, such as, for example, location (e.g., abdomen vs. back) or depth of sensor insertion.

In general, the sensor sensitivity functions can be created by theoretical or empirical methods, or both, and stored as functions or as look-up-tables, thereby allowing for sensor self-calibration that eliminates (or substantially reduces) the need for reference measurements. The sensor sensitivity functions can be generated at the manufacturing facility and shipped with the system or generated by the system shortly prior to (or during) use.

Calibration

Figure 5:
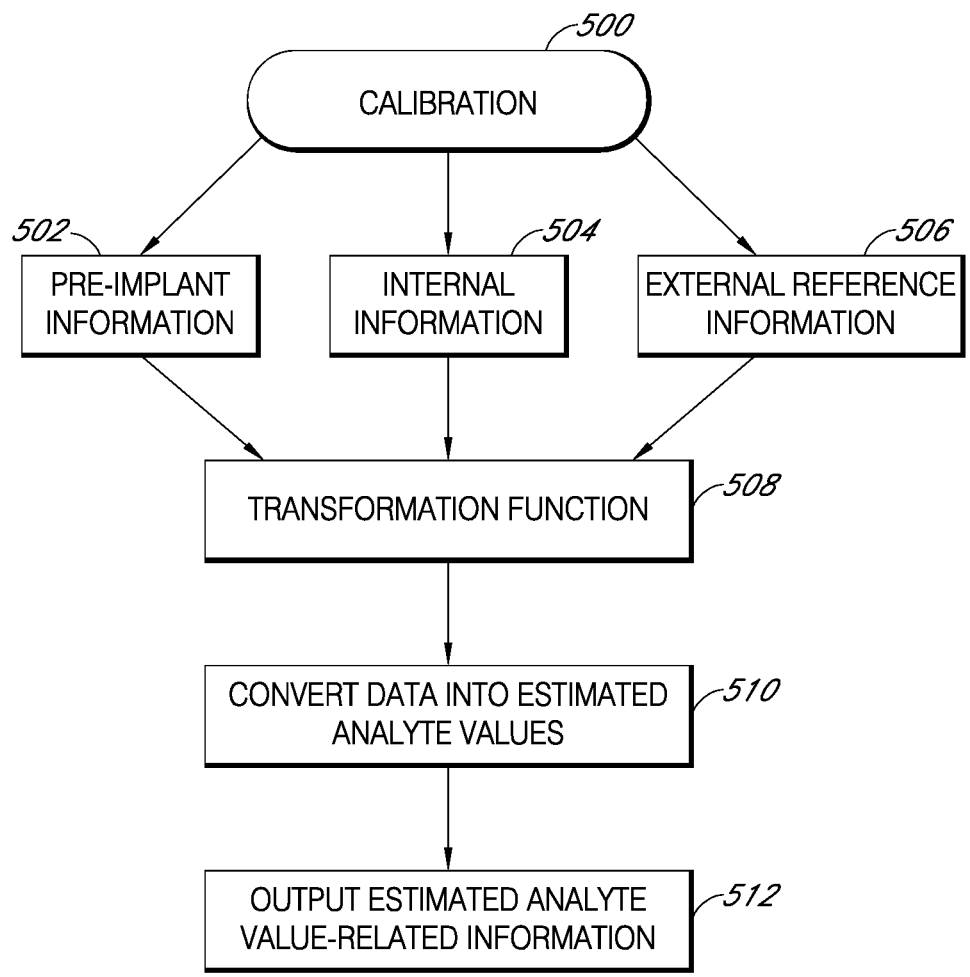
FIG. 5 illustrates a diagram of a calibration process that uses various inputs to form a transformation function in accordance with an embodiment.

An exemplary calibration process in accordance with some embodiments will now be discussed with reference to FIG. 5. FIG. 5 illustrates an example calibration process 500 that can use one or more of pre-implant information 502, internal diagnostic information 504 and external reference information 506 as inputs to form or modify a transformation function 508. Transformation function 508 can be used to convert sensor data (e.g., in units of current or counts) into estimated analyte values 510 (e.g., in units of analyte concentration). Information representative of the estimated analyte values can then be outputted 512, such as displayed on a user display, transmitted to an external device (e.g., an insulin pump, PC computer, mobile computing device, etc.) and/or otherwise processed further. The analyte can be glucose, for example.

In process 500, pre-implant information 502 can mean information that was generated prior to implantation of the sensor(s) presently being calibrated. Pre-implant information 502 can include any of the following types of information:

A priori information including sensitivity values and ranges from in vitro or in vivo testing; predetermined sensitivity profile(s) associated with the currently used (e.g., implanted) sensor, such a predicted profile of sensitivity change over time of a sensor;

previously determined relationships between particular stimulus signal output (e.g., output indicative of an impedance, capacitance or other electrical or chemical property of the sensor) to sensor sensitivity (e.g., determined from prior in vivo and/or ex vivo studies) such as described in US Patent Publication 2012-0265035, which is incorporated herein by reference in its entirety;

previously determined relationships between particular stimulus signal output (e.g., output indicative of an impedance, capacitance or other electrical or chemical property of the sensor) to sensor temperature (e.g., determined from prior in vivo and/or ex vivo studies);

sensor data obtained from previously implanted analyte concentration sensors, such as sensors of the same lot of the sensor being calibrated and/or sensors from one or more different lots;

calibration code(s) associated with a sensor being calibrated;

patient specific relationships between sensor and sensitivity, baseline, drift, impedance, impedance/temperature relationship (e.g., determined from prior studies of the patient or other patients having common characteristics with the patient);

site of sensor implantation (abdomen, arm, etc.) specific relationships (different sites may have different vascular density);

time since sensor manufacture (e.g., time sensor on shelf, date when sensor was manufactured and or shipped, time between when the sensor was manufactured and/or shipped and when the sensor is implanted); and exposure of sensor to temperature, humidity, external factors, on shelf.

In process 500, internal diagnostic information 504 can mean information generated by the sensor system in which the implanted analyte sensor (the data of which is being calibrated) is being used. Internal diagnostic information 504 can include any of the following types of information:

stimulus signal output (e.g., the output of which can be indicative of the sensor's impedance) of sensor using any of the stimulus signal techniques described herein (the stimulus signal output can be obtained and processed in real time);

sensor data measured by the implanted sensor indicative of an analyte concentration (real-time data and/or previously generated sensor data using the currently implanted sensor);

temperature measurements using the implanted sensor or an auxiliary sensor (such as a thermistor) co-located with the implanted analyte sensor or separately from the implanted analyte sensor;

sensor data from multi-electrode sensors; for example, where one electrode of the sensor is designed to determine a baseline signal;

sensor data generated by redundant sensors, where one or more of the redundant sensors is designed to be substantially the same as at least some (e.g., have the same sensor membrane type), if not all, of the other redundant sensors;

sensor data generated by one or more auxiliary sensors, where the auxiliary sensor is having a different modality such (as optical, thermal, capacitive, etc.) co-located with analyte sensor or located apart from the analyte sensor;

time since sensor was implanted and/or connected (e.g., physically or electronically) to a sensor electronics of a sensor system;

data representative of a pressure on sensor/sensor system generated by, for example, a pressure sensor (e.g., to detect compression artifact);

data generated by an accelerometer (e.g., indicative of exercise/movement/activity of a host);

measure of moisture ingress (e.g., indicative of an integrity of a moisture seal of the sensor system); and a measure of noise in an analyte concentration signal (which can be referred to as a residual between raw and filtered signals in some embodiments).

In process 500, external reference information 506 can mean information generated from sources while the implanted analyte sensor (the data of which is being calibrated) is being used. External reference information 506 can include any of the following types of information:

real-time and/or prior analyte concentration information obtained from a reference monitor (e.g., an analyte concentration value obtained from separate sensor, such as a finger stick glucose meter);

type/brand of reference meter (different meters can have different bias/precision);

information indicative of carbohydrates consumed by patient;

information from a medicament pen/pump, such as insulin on board, insulin sensitivity, glucagon on board;

glucagon sensitivity information; and information gathered from population based data (e.g., based on data collected from sensors having similar characteristics, such as sensors from the same lot).

Detection of Outliers

A beneficial feature of calibration is the ability to determine the presence of outlier data points or outliers in the calibration information (e.g., matched data pairs in the calibration set). As is easily appreciated, the inclusion of poor data points, such as reference glucose outliers, may influence any calibration in a negative fashion, e.g., create a bias or error in the calibrated sensor data derived from error from the calibration information. For example, errant finger sticks are an obvious source of poor reference data points. Errant finger sticks originate from different sources including user error and sensor-BG mismatch.

Examples of user error include errant entry into receiver (e.g., 109 mg/dl vs. 190 mg/dl) and poor finger stick technique (e.g., "sugar on the finger"). Examples of sensor-BG mismatch include time lag and the sensor not tracking (e.g., BG trending up, sensor trending down).

Errant calibrations may result in a poorly drawn calibration line, and resulting error in the transformation function used to convert the sensor-generated data into clinical units. Consequently, the ability to identify and/or remove or reduce the presence of outliers ensures that the calibration set carried forward is more accurate, thus yielding a more accurate calibration line.

Figure 6:
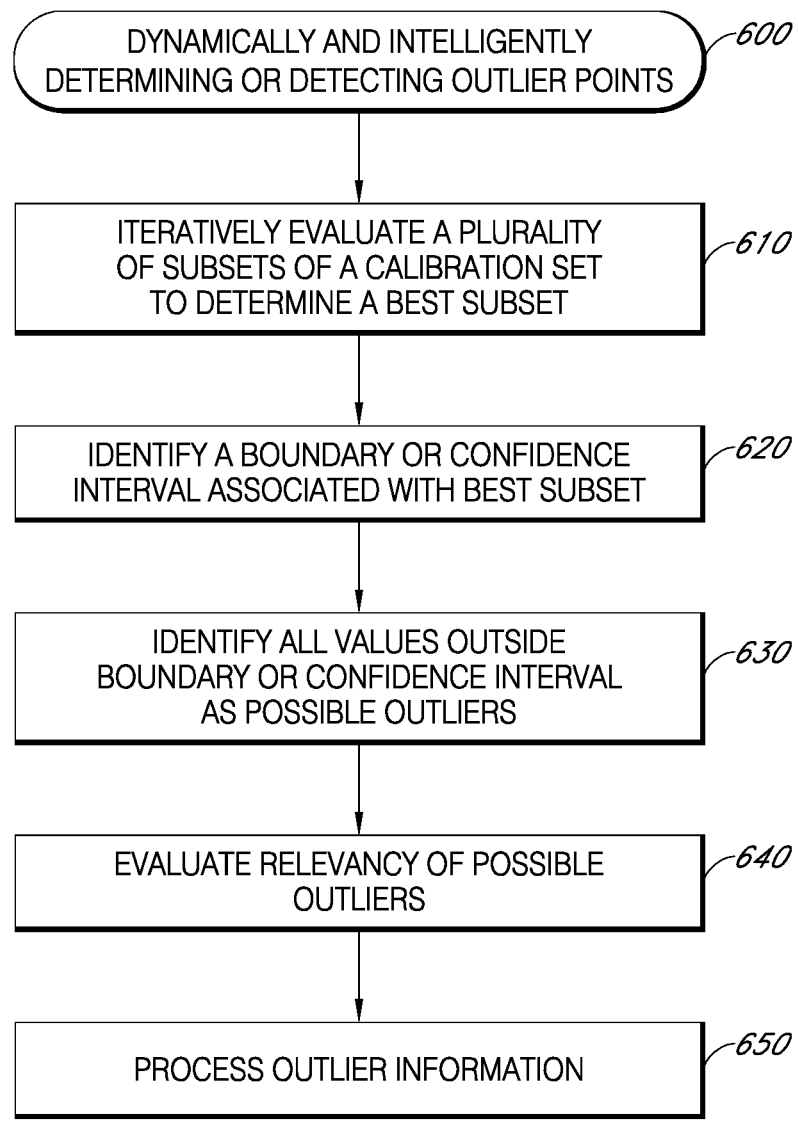
FIG. 6 illustrates a flowchart describing a process for dynamically and intelligently determining or detecting outlier matched data pairs in accordance with an embodiment.

FIG. 6 is a flowchart 600 illustrating a process for dynamically and intelligently determining or detecting outlier data points in accordance with an embodiment of the disclosure. External BG reference data (e.g., blood glucose values from finger stick checks) may or may not be useful in calibration, depending on the amount error associated therewith and/or the reason for any error or discrepancy between the BG reference data and time corresponding sensor data. As explained above, detecting outlier data points is highly desirable as the exclusion of such data points may minimize and/or prevent error in sensor calibration, making calibration more reliable.

At block 610, a processor module may be configured to iteratively evaluate a plurality of subsets of data in the calibration data set. In some embodiments, the processor module determines the best subset of data from the calibration data set. In general, the iterative evaluation includes iteratively evaluating different calibration data from a single calibration set during a particular calibration or iteratively evaluating different calibration data from a collective calibration set at different calibrations, whereby trends in error may be identified.

In some embodiments, a subset can be at least 1/N of the matched data pairs, or be between 0.5*N and N−1, where N is the number of matched data pairs in a full set. In some embodiments a subset can be at least ½ of the matched data pairs. In some embodiments, the calibration data set will include at least 5 matched data pairs; however, some calibration data sets will include 10 or more matched data pairs. As used herein, the data points in the calibration data set may include matched data pairs, which include a reference data value (e.g., BG value) and a sensor data value (e.g., counts).

In some embodiments, it may be advantageous to reduce the number of subsets that that are evaluated in order to improve computational efficiency. For example, heuristic methodologies may be applied by using prior information (e.g., information from previous outlier detection evaluations) to better identify best data pairs (or subsets) and/or worst data pairs (or subsets). In other words, trends or history associated with each match data pair or subset may be used to limit the iterative evaluation of subsets. Advantageously, the heuristic approach to determining which subsets to evaluate takes advantage of the fact that the matched pairs in the subset used in the previous iterations represent points that are close to the regression line; this is expected to yield good results in spite of the reduction in the number of subsets examined. One heuristic methodology includes "pre-screening" the newest BG value by comparing a newly formed matched data pair to the best subset determined from the previous iteration of outlier detection; this may allow an immediate decision to be made prior to full iterative processing.

In some embodiments, matched data pairs may be assigned weights based on a likelihood of being an outlier. The processor module may use any subset and compute the residuals, after which each point may be assigned a weight based on how far the point is from the line (e.g., the residual). These weights may be combined in a way to signify how likely this point is to be an outlier. For example, the lower the weight is, the better the point fits with the rest of the matched pairs or vice versa. For example, the weights can be the average of the squares of the residuals obtained from all the subsets on which it was evaluated. In some embodiments, the processor module may use the only the subsets with the lowest weights (e.g., below a threshold), effectively choosing the points that are best correlated with most other points.

In some embodiments, each subset can be used to draw a line (e.g., using regression analysis). In some embodiments, a plurality of lines associated with the data sets is generated to determine the best subset. For example, generating a plurality of lines may result in a best line associated with the best subset. In some embodiments, the best line comprises a line that has the best fit for all points used to generate the line. The best fit may be determined using a one or more functions selected from the following list: For example, regression techniques useful for determining statistical associations of data sets, such as, linear regression (e.g., Least Quantile of Squares ("LQS"), Least Trimmed of Squares ("LTS")), non-linear regression, rank correlation, least mean square fit, mean absolute deviation, and mean absolute relative difference, or the like may be used.

In some embodiments, each subset defines a convex hull or convex envelope. In some embodiments, a plurality of convex envelopes associated with the data sets is generated to determine the best subset. For example, generating a plurality of convex envelopes may result in a best convex envelope associated with the best subset. In some embodiments, the best convex envelope comprises a convex envelope that has the best fit for all points used to generate the convex envelope. The best fit may be determined using some standard algorithm for convex hull computation such as one or more functions selected from the following list: convex hull algorithms such as Graham scan (e.g., O(N log N) complexity), QuickHull (e.g., O(N log N) average complexity), and Monotone chain (e.g., O(N log N)) and/or rotating calipers algorithm for computing the diameter and width of a convex hull (e.g., (O(N) time once the convex hull is computed).

In some embodiments, using a convex hull according to a first heuristic to reduce the number of subsets is desirable because any outliers or outlier data points will be on the convex hull (e.g., be part of the line defining the convex hull). Thus when considering the subsets, the convex hull (which takes N log N times) can be constructed, and only subsets that are completely inside the convex hull may be used to draw a calibration line. Once a calibration line is drawn, points on the hull may be included one by one into the subset, each time using the point closest to the current line. If, after including a sufficient number of points, any of the remaining points on the convex hull are found to be far from the line, such points can be singled out as outliers.

At block 620, the processor module may be configured to identify a boundary or confidence interval associated with a best subset. In some embodiments, the boundary or confidence interval may be the boundary lines of the best convex envelope.

In some embodiments, the boundary or confidence interval of step may be an acceptable deviation or scatter from the best line. For example, each point used to generate the best line may be compared against the best line to determine the residual value (e.g., the most accurate points relative to the best line) for each point. In some embodiments, the boundary or confidence interval is a predetermined multiple of the scale. The scale is herein defined as the average value of the residuals multiplied by some consistency factor. The boundary interval may then be defined as the average residual multiplied by a consistency factor (e.g., multiplied by a factor like 2). In other embodiments, the boundary or confidence interval is a set value, e.g., may be preset as part of factory settings. In some embodiments, the boundary or confidence interval is calculated and updated in real-time. Thereafter, the residual value for each point may be compared against the boundary or confidence interval to determine if the residual value for each point falls within the boundary or confidence interval.

In some embodiments, the diameter and width of the convex hull may be computed using a second heuristic. As used herein, the diameter is the maximum distance between two points in the convex hull and the width is the minimum distance between two parallel lines of support. Generally, the points in a set will cluster around a line if the diameter is much larger than the width. In some embodiments, the ratio of the area of the convex hull to the diameter may be compared. In some embodiments, walking through the points on the convex hull and finding the residuals with respect to the diameter, may identify any point outside a given residual as an outlier.

At block 630, the processor module may be configured to identify all values (e.g., data points) outside the boundary or confidence interval as possible outliers. For example, if any residual value falls outside the boundary or confidence interval, then each point associated with the residual value that falls outside the boundary or confidence interval may be identified as a possible outlier.

A few examples of methods for performing blocks 610 through 630 are provided, below:

Example 1: Least Quantile of Squares ("LOS")

In one exemplary embodiment, the Least Quantile of Squares ("LQS") or Least Median of Squares ("LMS") robust regression technique allows for discrimination of contaminated data from 0% to 50%, meaning outliers may be detected if up to 50% of the data is contaminated. For example, the highest breakdown value LQS may have is 50% because it is at this point that e.g., the good data becomes indiscernible from bad data. LQS may be thought of as a sampling algorithm (e.g., it tries all permutations in a calibration data set to draw lines). Ultimately, LQS operates by minimizing the residual around a desired quantile.

Example 2: Least Trimmed of Squares ("LTS")

In another exemplary embodiment, the Least Trimmed of Squares ("LTS") is a robust statistical method that fits a function to a set of data without being impacted by outliers.

In some exemplary embodiments, a modified version, such as the FAST-LTS algorithm may be used. The function first calculates all possible line combinations of based on subsets of the calibration set (e.g., if the calibration set has 6 points then one of the lines may be drawn using points 1, 3, 4, 6) as shown below:

$$\text{\# of Possible Combos} = \frac{N!}{(N-h)! \cdot h!}$$

If there are six points in the calibration set, then the # of lines drawn will be 15. In some exemplary embodiments, the FAST_LTS algorithm begins with all 2-point combinations and then adjusts the line in a way to encompass h points. In some embodiments, the FAST_LTS algorithm may start with all h-point combinations. In some embodiments, where the calibration data is sparse, there is no advantage in terms of computational efficiency between starting with 2 points or h points. Note that h can be any number as long as it satisfies $0.5*N < h < N-1$.

Figure 7:
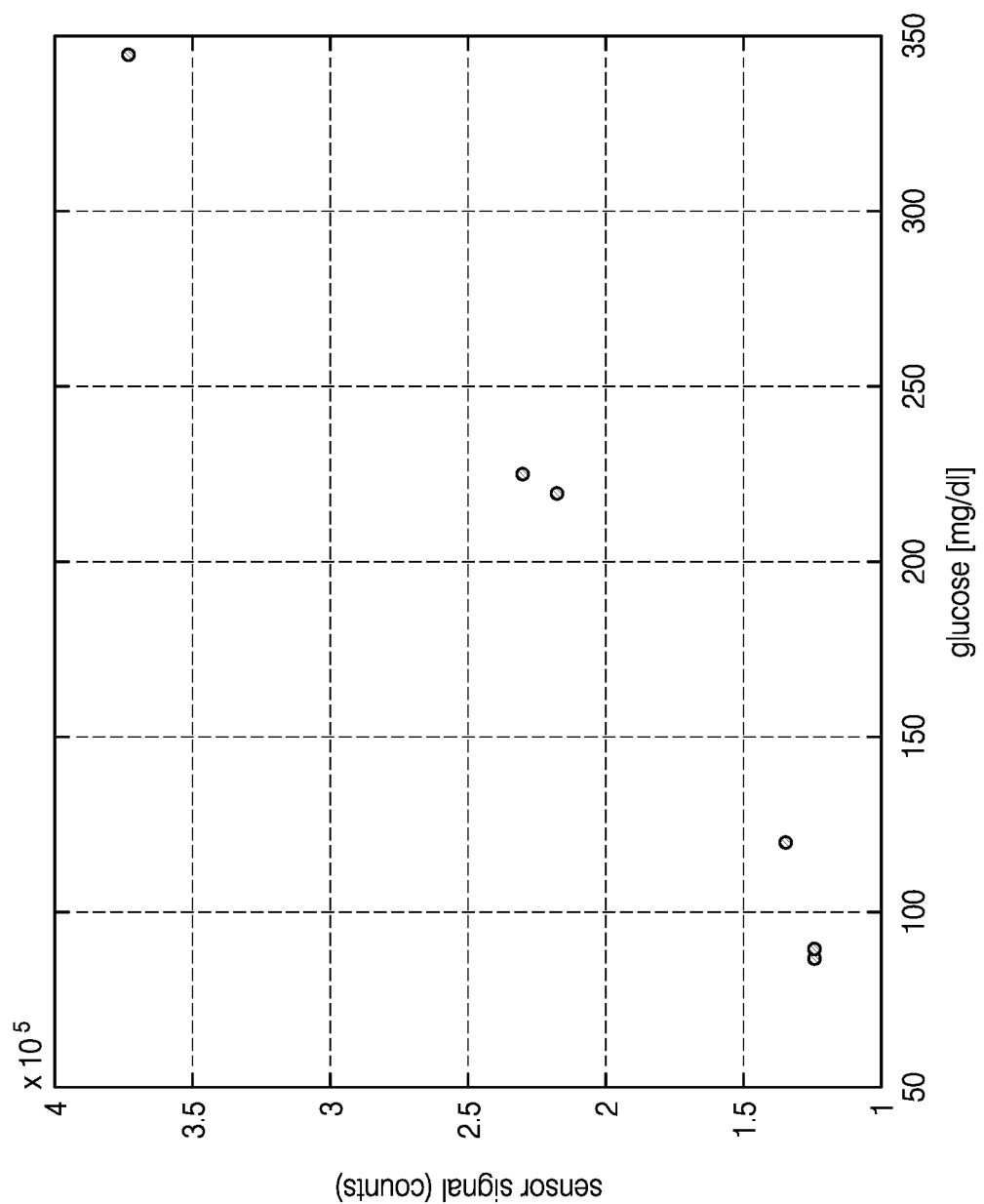
FIG. 7 illustrates a diagram of a calibration set having 6 matched data pairs in accordance with an embodiment.

In some embodiments, in order for the function to run, the calibration set must have 5 or more points; however, the input to the function could be a subset of the calibration set (e.g. all points in the last 48 hours if there are at least 5 or more, or the last 5 points entered into the device in the event the sensor goes out of calibration). Once all h-point combinations are calculated, the function loops through and calculates an Ordinary Least Squares ("OLS") line with each h-point combination. In other words, even though there are 6 points in the calibration set, only 4 of those are used to calculate the line. An example of a 6 point calibration set (FIG. 7) and one of the OLS lines drawn (FIG. 8) using h-points are provided.

Figure 8:
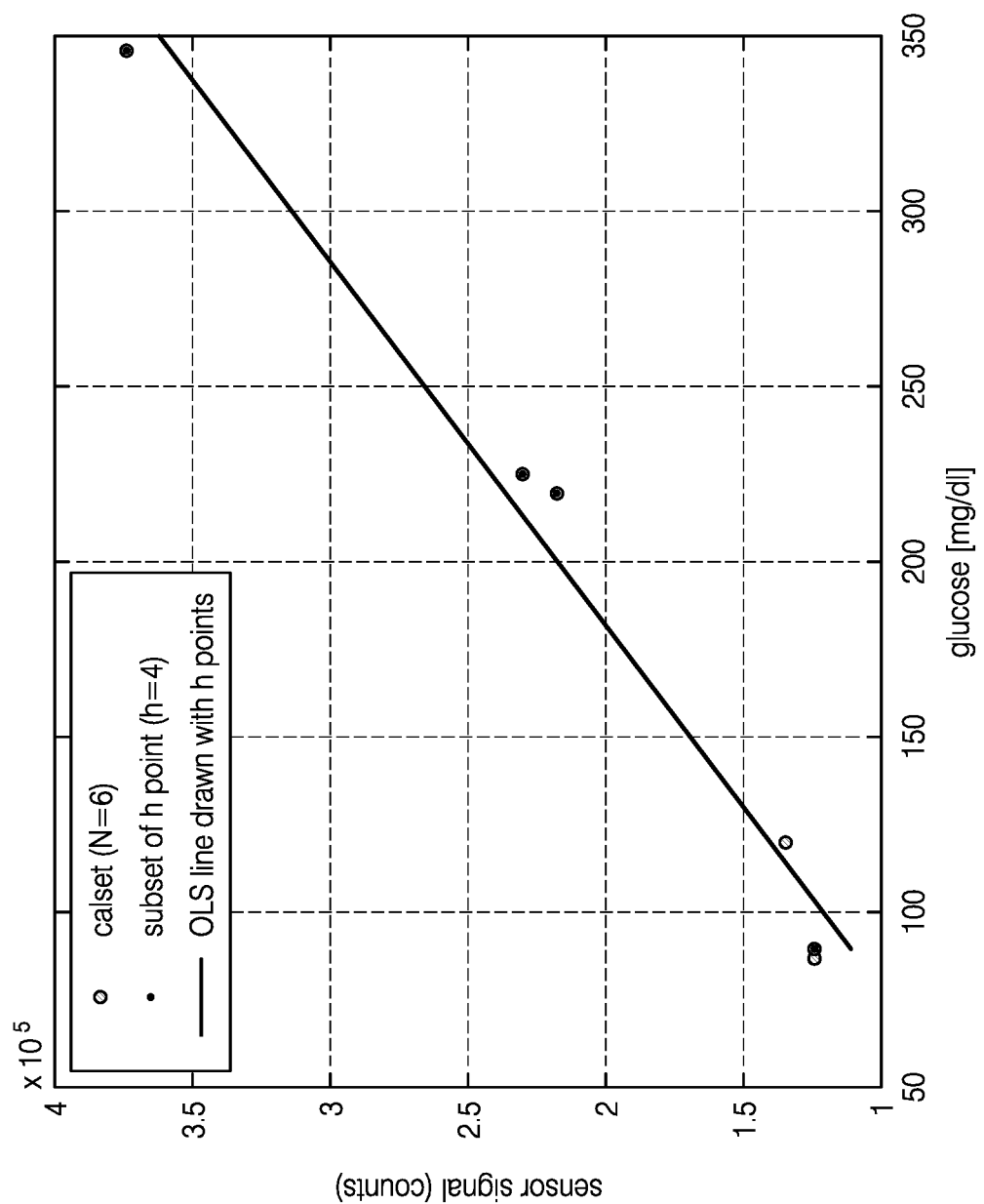
FIG. 8 illustrates a diagram of a calibration line drawn using Ordinary Least Squares ("OLS") in accordance with an embodiment.

Still referring to FIG. 8, each line can be bounded by one or more acceptable boundaries for slope and baseline that may be static or dynamic. In some embodiments, the boundaries may include confidence intervals. In some embodiments, the acceptable boundaries include an upper and lower boundary defined by minimum and maximum slopes and baselines, against which certain calibration information (e.g., calibration line and/or matched pairs) are compared.

An estimate of the expected signal may be calculated using all the BG values in the calibration set and a regression line drawn. The residuals in the signal (raw data points) may be calculated, and then the absolute value of each of the residuals may be taken and then sorted from smallest to largest. When using a wedge parameter, if there is no line that fits within the wedge parameter, the function exits because there are no realistic lines being drawn. In some embodiments, information related to a failure to pass the wedge parameters may be used to drive a change in the limits used in the processor module or the wedge parameters or to communicate with algorithms of the system (e.g. calibration algorithms) to suggest that some points in the calibration set need to be dropped.

In some embodiments, once the optimal line is selected, the residuals may be calculated, squared and then sorted from smallest to largest, thereby enabling an estimate of the scale (dispersion around the line) to be calculated. The scale value is greater than 0, but it could be bounded by another value greater than 0 (e.g. a low limit, a high limit, or both) to avoid further calculations seen below. For example, if the high limit of the scale is consistently getting hit (e.g. scale>high limit), such information may be communicated with other algorithms of the system (e.g. calibration) because such information may be indicative of too much scatter in the calibration set, that the calibration set is not linear enough and/or that one or more data pairs should be removed. Having calculated the scale, an estimate of possible outliers (in counts) can be made. All points whose ratio of residual to scale exceeds a threshold (e.g. residual$_i$/scale>2.25) may be flagged as an outlier. One or more levels of scales (e.g., preliminary, intermediate and final scales) may be calculated and processed as described above. Other diagnostics may be applied to the scale(s) to improve accuracy as is appreciated by one skilled in the art.

In some embodiments, the possible outliers may be removed from the calibration set immediately. In some embodiments, the possible outliers may be removed from the calibration set retrospectively at some calibration after the calibration that resulted in the flagging. In some other embodiments, the flagging of possible outliers may signal the algorithm to check for clinical relevancy of the error before removing the point(s) from the calibration set. In some other embodiments, only the relevancy of the error may be used to remove points from the calibration set.

Referring now to block 640, the processor module may be configured to evaluate the relevancy of possible outliers identified at block 630 to determine a clinical relevancy of, to discriminate the root cause of the error in the possible outlier, trends of outlier information, or the like, resulting in outlier information useful for further processing (block 650). Although some embodiments for flagging potential outlier points are described above (blocks 610-630), relevancy evaluation (640) and responsive process (650) may be combined or applied with any methodology for determining outlier information. While not wishing to be bound by any particular theory, errors that cause the flagging of possible outliers may be caused by a variety of different situations. For example, a phenomenon that may be described as "dip and recover," which occurs during early implantation of a subcutaneous sensor, may be determined. As another example, physiological changes in the compartments of the test samples (e.g., capillary blood vs. interstitial fluid) may be inherently different at certain times. Additionally, the error may be flagged as an outlier based on the statistical analysis or residuals as evaluated in raw counts, but the error may not be clinically relevant, for example, the error in the blood glucose reference value compared regression line (best line or calibration line) captures clinical error.

In some embodiments, the processor module may evaluate the possible outliers only when the most recent BG is determined to be a possible outlier. In some embodiments, the relevancy determination includes examining one or more factors from the following list, including but not limited to: time since sensor implant, trends in outlier evaluation, the amplitude of error of a data point relative to the (best) line (e.g., evaluated in clinically relevant units such as mg/dL or mmol/L), the direction of error a data point relative to the (best) line (e.g., the direction of the error is less than 0 or greater than 0 when BG reference value is reading higher than sensor value or lower than sensor value, respectively, which may be evaluated in clinically relevant units), a clinical risk of the data (e.g., static or dynamic risk) at the time stamp of the matched data pair, a rate of change of the analyte concentration or derivative of the sensor data associated with the matched data pair, a rate of acceleration (or deceleration) of the analyte concentration or second derivative of the sensor data associated with the matched data pair, or the like. In some embodiments, the relevancy determination evaluates an influence of the possible outlier on the regression line (best line or calibration line). For example, sometimes in regression analysis, a data point has a disproportionate effect on the slope of the regression equation. One way to test the influence of an outlier is to compute the regression equation with and without the outlier; a threshold may be applied, such as greater than 25 pA/mg/dL, to determine whether the influence is disproportionate.

In some embodiments, the check for relevancy may be performed because a highly correlated calibration set may flag a point as a statistical outlier but the blood glucose may be, e.g., only 5 mg/dl off the line, which is well within the error of standard blood glucose meters. For example, a clinical relevance may be calculated based on an estimated glucose value ("EGV"), which also may referred to as calibrated glucose value, as shown below:

$$EGV = \frac{(Counts_i - b)}{m}$$

The EGV may then be checked against the matched BG. In some embodiments, if the matched BG is less than or equal to a predetermined threshold, such as ≤75 mg/dl, then the error check utilizes a first criterion, such as an absolute difference and if the matched BG is greater than a predetermined threshold, such as >75 mg/dL, then the error check utilizes a second criterion (different from the first), such as an absolute relative difference ("ARD"). In one exemplary embodiment, if the error check is an absolute difference (BG≤75 mg/dl), then the threshold for the error is 20 mg/dl (~3 sigma of BG error threshold) and if the error check is an ARD (BG>75 mg/dl) then the error threshold is 25% (~3 sigma of BG error threshold). Other thresholds and metrics known to those of skill in the art may be applied. As a result of the clinical relevancy determination, it may be determined that the error associated with the possible outlier is not clinically relevant and the matched data pair may remain in the calibration set. For example, if the calculated error is within predetermined thresholds, then the point initially identified as a possible outlier (e.g., using a statistical analysis of error in the y-direction) may be re-identified as clean.

However, if the result of the relevancy determination test is a determination that the error is relevant, then processing may move to block 650. For example, the relevancy determination test may compare a parameter associated with the error described above against a quantitative outlier criterion (e.g., threshold), wherein errors that meet the criterion for clinically relevant outliers (e.g., outside a predetermined threshold) are flagged in outlier information.

In some embodiments, the relevancy determination test evaluates additional criteria, such as time since implant, since time since implant may be indicative of phenomena known to occur during the life of the sensor. For example, transcutaneous and implantable sensors are affected by the in vivo properties and physiological responses in surrounding tissues. For example, a reduction in sensor accuracy following implantation of the sensor is one common phenomenon commonly observed. This phenomenon is sometimes referred to as a "dip and recover" process. Although not wishing to be bound by theory, it is believed that dip and recover is triggered by trauma from insertion of the implantable sensor, and possibly from irritation of the nerve bundle near the implantation area, resulting in the nerve bundle reducing blood flow to the implantation area. Alternatively or additionally, dip and recover may be related to damage to nearby blood vessels, resulting in a vasospastic event. Any local cessation of blood flow in the implantation area for a period of time leads to a reduced amount of glucose in the area of the sensor. During this time, the sensor has a reduced sensitivity and is unable to accurately track glucose. Thus, dip and recover manifests as a suppressed glucose signal. The suppressed signal from dip and recover often appears within the first day after implantation of the signal, most commonly within the first 12 hours after implantation. It is believed that dip and recover normally resolves within 6-8 hours. Identification of dip and recover can provide information to a patient, physician, or other user that the sensor is only temporarily affected by a short-term physiological response, and that there is no need to remove the implant as normal function will likely return within hours. In one example, a combination of suppressed signal (e.g., detection of downward shift in sensor sensitivity) during a predetermined time period (e.g., during the first 36 hours after implantation) may be used to identify the root cause of the outlier as the dip and recover phenomenon.

Other physiological responses to the implantable sensor can also affect performance of the implantable sensor. For example, during wound healing and foreign body response, the surface of the implantable sensor can become coated in protein or other biological material to such an extent that the sensor is unable to accurately track blood glucose. This phenomenon is sometimes called "biofouling" and biofouling often manifests itself as a downward shift in sensor sensitivity over time. Similarly, the implantable sensor can become encapsulated by biological material to such an extent that the sensor is unable to provide glucose data, and the sensor is considered to effectively be at end of life. In some cases, the implantable device can be programmed to correct for errors associated with biofouling and end of life, so that identification of these phenomenon aids in providing more accurate glucose data. In one example, a combination of downward rate of change of sensor sensitivity over a predetermined time period (e.g., at least 5 days after sensor implantation) may be used to identify the root cause of the outlier as related to bio-fouling or end of life.

Another physiological affect that has been observed may be referred to as a "compartmental effect." This effect results from differences in actual physiological glucose levels in different compartments in the body, for example in capillary blood as compared to interstitial fluid. Identification of these physiological phenomena also generally provides information useful in determining whether the error associated with the flagged outlier is related to the reference BG value or the sensor data, and may be processed responsive thereto. Identification may include additional input, such as time since implant and/or timing, location and/or amount of insulin injected. In one example, when the host's rate of change of glucose exceeds a threshold and/or a meal has been recently consumed, and when outlier does not follow a trend of similar errors, the processor module may identify the root cause as a transient compartmental effect.

Other factors that may be evaluated to identify the root cause of the outlier may include secondary (e.g., redundant) sensors, trend information associated with outliers (outlier information) from previous iterations of outlier detection, or the like. Trend information may be particularly useful where a data point (matched pair) has been consistently showing a particular error mode, perhaps not with sufficiency to meet the outlier criteria of the evaluation block 630, but perhaps with enough sufficiency based on trend criteria (exceeding a threshold for x consecutive outlier evaluations, such as 2, 3, 4, 5, 6, 7 or 8). In general, any number of conditions and/or criteria may be evaluated to determine the relevancy (e.g., root cause and/or clinical relevancy) of the possible outlier.

At block 650, the processor module may be configured to process data responsive to outlier information determined at block 640. In general, matched data pairs flagged as outliers (outlier information) after the relevance determination test (block 640) may then go through additional processing. The outlier may be removed temporarily or permanently from the calibration set, prospectively or retrospectively. An outlier may be processed accordingly to block 650 with or without the relevance determination check of block 640 and/or may be iteratively processed at each outlier detection check. Additionally or alternatively, other data, such as information transmitted to an insulin delivery device, prompts on the user interface, or other related processing may be included herein.

In one example, when a series of iterations of outlier detection indicate a trend of sensor error, the processor module may increase the number of reference data requested and/or relied up on for calibration, for example when bio-fouling and/or sensor end of life is detected, as described in more detail elsewhere herein. In another example, when a series of iterations of outlier detection indicate a trend of reference blood glucose error, the processor module may decrease the number of reference data and/or not rely on reference data for sensor calibration, for example, when the sensor has stabilized and shows no signs of drift of sensor sensitivity. Such processing may allow the continuous glucose sensor system to switch between more or less (or no) reliance on blood glucose reference measurements based on the measure of accuracy of the sensor data versus the reference blood glucose measurements over time.

For example, the processor module may flag an outlier, but keep the flagged outlier in the calibration data set until the next data point is collected. In such an example, the flagging of the outlier enables an iterative process to confirm (or deny) the outlier based on additional data, such as the next reference data point and resulting matched data pair, to avoid false positive identification of outliers and resulting consequences to the user experience. In other words, when an outlier is flagged, the root cause of the outlier could be related to either the sensor data point or the reference data point (BG), since the flagged outlier would be influenced by both the sensor and the reference input. In some embodiments, when the next reference data point is input (after a flagged outlier), its respective matched data pair may confirm that the sensor performance is changing and the flagged outlier(s) is/are actually more reliable that the other matched data pairs in the calibration set, resulting in the removal of some or all other data pairs in the calibration set except the two flagged outliers and/or most recent matched data pairs. On the other hand, the next matched data pair (after flagging of an outlier) may not be identified as an outlier, and thereby confirm that the previously flagged outlier should be removed from the calibration set. Criteria for evaluating the next matched data pair with respect to a previously flagged outlier may include an iterative process as described herein with respect to dynamically and intelligently determining or detecting outlier data points (600) or using other criteria and analysis specific to determining the root cause and/or subsequent interpretation of the flagged outlier.

In one embodiment, if the most recent BG reference value is identified as a possible outlier (block 630), then the direction of the error is checked using a clinical relevancy test (block 640). For example, if the direction of the error is less than 0 (e.g., BG reference value is reading higher than sensor value), then at block 650, all points flagged as outliers, except for the most recent BG reference values, are removed from the calibration set. On the other hand, if the most recent BG reference value is identified as a possible outlier, and the direction of the error is checked using the clinical relevancy test is positive (e.g., sensor value higher than BG reference value), then no points are removed from the calibration set. Other methods for inclusion and/or exclusion of matched data pairs may be used to complement and/or supplement outlier detection methods described in flow chart 600.

This embodiment utilizes a clinical relevancy test that takes into account the direction of the error associated with a particular BG reference value (e.g., the matched data pair that includes the BG), whereby when the most recent BG reads higher than the sensor value, then it is assumed that the sensor is tracking well and the BG is contaminated due to user error, e.g., "sugar on the finger," and whereby when the sensor value reads higher than the BG value by a threshold, it is assumed that the BG was flagged as an outlier because of drift (e.g., change in sensitivity of the sensor over time). In such embodiments, the calibration set may be culled to remove poor data points (e.g., criteria that ensures at least about ½, ⅔ or ¾ of the matched data pairs in the calibration data set are removed). With a clean calibration set, the calibration line may be drawn using one or more preferred functions. If the system goes out of calibration, a modified process of outlier detection may be performed. As used herein, "out of calibration" refers to a state where sensor data is not converted due to lack of confidence in the calibration information. An exemplary modified outlier detection using a calibration set that does not include the BG value that caused the system to fall "out of calibration," may evaluate the following: A) if the most recent BG (BG1) is flagged as an outlier and BG1 reads higher than the sensor, then the calibration set (CAL1) before BG1 was entered is stored and the system waits for the next BG (BG2) to be entered. Once BG2 is entered, it is passed into outlier detection with CAL1. If BG2 is flagged as an outlier, then CAL1 is cleared and BG1+BG2 is made the new calibration set (CAL2). If BG2 is clean, BG1 is thrown out and CAL1+BG2 becomes the new calibration set (CAL2') and B) BG1 is reading lower than the sensor, then the calibration set is cleared and BG1 is stored the system waits for a new BG to start a new calibration set.

In some embodiments, information associated with the flagged outlier may be transferred to another algorithm of the system and/or used to trigger another algorithm of the system. For example, an outlier may be particularly identified as being indicative of a downward sensitivity shift meeting a criterion (e.g., based on an analysis of the error between the BG and corresponding EGV of the matched pair), such information may be a risk factor indicative of end of life and may be used as an input into the end of life determination function and/or may initiate the end of life algorithm. As another example, an outlier may be particularly identified as being associated with a "dip and recover" event based on time since implant, the host's history with continuous glucose sensing and/or the like. Accordingly, this information may be useful by the processor module to trigger a suspend of the glucose data for a predetermined time period (e.g., "Dip and recover" known to have a finite time period) and/or to inform the user on the user interface that certain implantation effect may cause some inaccuracies for the next x number of minutes or y number of hours (e.g., 2, 4, 6, 8, 10, 12, 16 or 24 hours).

In some embodiments, interaction of the host with the device may be useful input, which together with the knowledge of the flagged outlier, may be indicative of a user's frustration with the device and/or the host may require additional guidance. In some embodiments, when the host is regularly entering BG values (e.g., outside of a normal calibration scheme) at a rate that is more than periodically (e.g., more than X BG entries in the last Y minutes, for example more the 2, 4, or 6 entries in the last 15, 30 or 60 minutes), then it may be an indication that the host is noticing an error and may be trying to correct the sensor by "feeding" BG values to the device. The resulting processing may include trusting the BG values and providing feedback in the form of messages and/or glucose values that shows the host that the device is receiving and responding to the BG inputs. One example may include asking the host questions through prompts on a user interface to determine the root cause. Another example may include considering trusting the user's input more than the outlier detection test and thereby "unflagging" the outlier temporarily or permanently so that the so-called flagged outlier will actually influence the estimated glucose values displayed to a user, temporarily or permanently, so as to appear to more closely align with his/her BG reference values.

If the most recent BG is not flagged as an outlier, it can be assumed outlier detection ran successfully and the outlier detection line (optimal OLS line) is within the wedge of the line logic function (the line drawing logic and outlier detection may have different wedges), then the system is in calibration and uses the line drawn by outlier detection.

In some embodiments, the processing responsive to outlier detection determines whether and/or how much pre-implant information 502, internal diagnostic information 504 and/or external reference information 506 may be relied upon for any given calibration. In one example, wherein a lack of confidence in reference glucose data resulting from iterative failures of matched data pairs to pass one or more evaluations of the processes of flow chart 600 (for previous calibrations) exists, the processor module may determine that calibration should rely solely pre-implant information 502 and/or internal diagnostic information 504. In some embodiments, the use of pre-implant information 502, internal diagnostic information 504 and/or external reference information 506 may be selected and/or selectively weighed based on the outlier detection process and/or other diagnostic information, such as internal diagnostic information. In some embodiments, depending on other parameters, such as time since implant, or historical sensor performance for a particular patient, the use of external reference information may be adaptively determined and applied to calibration. In one example, a sensor session may begin (initially calibrate) by relying solely on pre-implant information 502 (e.g., a priori sensitivity information), and subsequently rely more or less on the pre-implant information 502 as the sensor session progresses and additional internal diagnostic information 504 and/or external reference information 506 is obtained. In another example, the sensor session may rely at least partially on external reference information 506 during a sensor session, but adaptively rely less and less on the external reference information as the sensor session progresses and increased confidence in the pre-implant calibration information and/or internal diagnostic information is determined as the sensor session progresses. As another example, when pre-implant information in the form of patient historical information is available (i.e., because the patient has worn the sensor previously), the sensor may rely more on the pre-implant information during subsequent sensor sessions as compared to the first one or few sensor sessions. Other combinations and selective uses of pre-implant information 502, internal diagnostic information 504 and/or external reference information 506 for calibration of the sensor (i.e., adaptively and/or progressively over a sensor session) may be envisioned as well.

Referring back to flow chart 600, in one exemplary embodiment, iterative evaluations may be performed on an entire calibration set, for example using linear regression, rather than on a subset of the calibration set. Stated another way, either iteratively evaluating a plurality of subsets on a single calibration set during a particular calibration or iteratively evaluating the entire calibration set at different calibrations (which could also be considered subsets of all data pairs collected during a sensor session), the end result may be the same (e.g., looking for trends in error to confirm the clinical relevancy of the error). For example, traditional linear regression analysis (e.g., ordinary least squares ("OLS")) homoscedasticity is assumed. In other words, the standard deviations of the error terms are constant and independent of the x-value ($\varepsilon \sim N(0, \sigma)$). OLS may identify outliers through repetition of error.

It should be appreciated that block 610 covers the iterative evaluation of the certain matched data pairs at different calibrations. Block 620 recites: identify a boundary or confidence interval associated with a best subset. In some embodiments, based on the regression line (e.g., drawn from the calibration set or a subset of the calibration set), it may be possible and desirable to track which data pair(s) is consistently showing error above a threshold (e.g., trended with each calibration evaluation). For example, while there may not be enough error to know whether a data pair should be removed using a single evaluation, when looking at a trend of multiple calibration evaluations (e.g., iteratively over a day or two or more), the data pair(s) may show a consistent trend of error. The boundaries or confidence interval used to watch the trending of these may be the same or different from (e.g., less stringent than) the boundaries or confidence intervals associated with other aspects, such as the flagging of possible outliers. For example, at initialization, the system may start counting error and looking for frequency of error over time. Error may be calculated by using the slope (M) and intercept/baseline (B) to recalculate the EGV for each of the count values of each data pair in the calibration set. This may provide a normalized comparison for each data pair in the calibration set. With the BGs in the calibration set, the error in the EGV calculated may be determined, as shown below.

$$Error_i = 100 * \frac{|EGV_i - BG_i|}{BG_i}$$

This equation advantageously allows the error to be determined in units of blood glucose (and thus a better clinical relevancy of the error) for each data pair. In some embodiments, the relevancy may be determined based on a trending of error (e.g., data pair identified as possible outlier 5 out of the last 6 calibrations). In other words, both frequency of the error, and the fact that the error is being evaluated after conversion of the counts (for each data pair) into units of blood glucose, may be used to evaluate the relevancy (e.g., clinical relevancy) of the possible outliers. In this embodiment, when a data pair has been tracked with a clinical error (e.g., error in units of blood glucose) greater than a certain threshold for at least x of the last y calibrations/evaluations, it may be affecting the calibration error in a clinically relevant manner. In some embodiments, this "trending" error may be flagged e.g., as an outlier. In some embodiments, outliers or points identified to have some moderate level of error may be flagged). For example, this embodiment qualitatively says when a certain error has been seen frequently (x number of times in the past y amount of time) with the same data pair, the data pair is removed from the calibration set and a new calibration line (e.g., dummy version) is tested to determine if the new calibration line would pass other tests for accuracy in calibration (e.g., wedge parameters). If the new calibration line passes the tests or is as good as the last or is better than the last (e.g., based on predetermined criteria), then the removed data pair is permanently removed from the calibration set (e.g., culled or thrown out).

Detection of End of Life

Embodiments of glucose sensors described herein may have a useful life in which a sensor can provide reliable sensor data. After the useful life, the sensor may no longer be reliable, providing inaccurate sensor data. To prevent use beyond the useful life, some embodiments notify a user to change the sensor after it has been determined that the sensor should no longer be used. Various methods can be used to determine whether a sensor should no longer be used, such as a predetermined amount of time transpiring since the sensor was first used (e.g., when first implanted into a user or when first electrically connected to sensor electronics) or a determination that the sensor is defective (e.g., due to membrane rupture, unstable sensitivity or the like). Once it is determined that the sensor should no longer be used, the sensor system can notify a user that a new sensor should be used by audibly and/or visually prompting a user to use a new sensor and/or shutting down a display or ceasing to display new (or real-time) sensor data on the display, for example.

In some embodiments, continuous glucose monitors may show signs of sensor "end of life" near their end of life. The signs of end of life may be recognized and total sensor end of life and any resulting user safety or inconvenience may be prevented. In some embodiments, this disclosure describes distinct sensor failure signatures and how they can be reliably recognized and detected.

Figure 9:
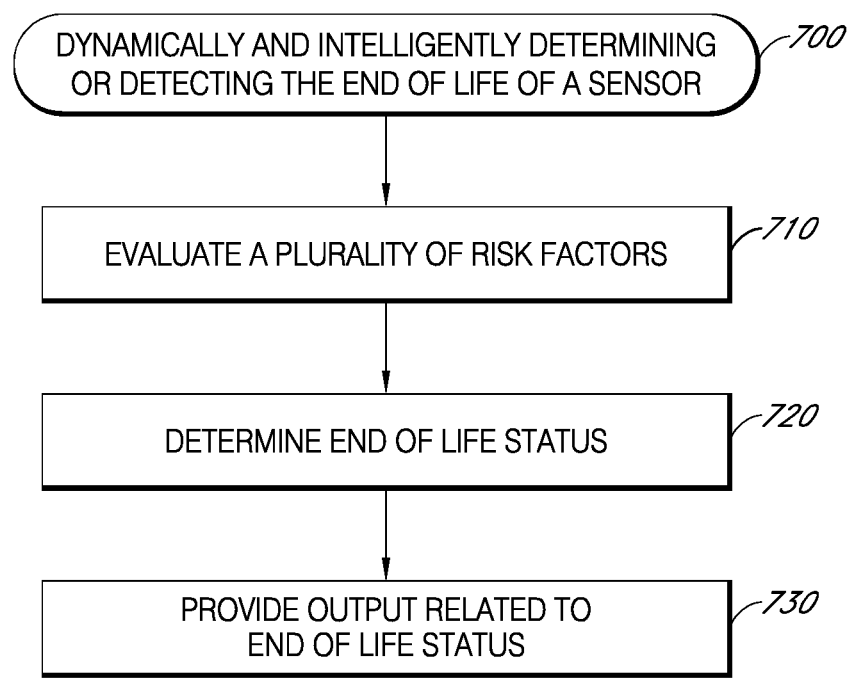
FIG. 9 illustrates a flowchart describing a process for dynamically and intelligently determining end of life for a sensor in accordance with an embodiment.

Referring to FIG. 9, a flowchart 700 illustrating a process for dynamically and intelligently determining or detecting the end of life of a sensor in accordance with an embodiment of the disclosure is shown. As explained above, detecting the end of life of a sensor is highly desirable as the accurate reading of a user's blood glucose level is important in diabetic monitoring.

At block 710, the processor module may be configured to evaluate a plurality of risk factors that may be indicative of sensor end of life, for example using an end of life ("EOL") risk factor instruction(s), algorithm(s) and/or function(s). In general, the processor module may include one or more functions that evaluate a plurality of individual risk factors that may each partially provide an indication of the end of sensor life. In general EOL symptoms are progressive, e.g., not all symptoms (or episodes) indicate sensor failure. Each of the risk factors may be evaluated periodically or intermittently as often as with the receipt of sensor data (e.g., every 5 minutes) or more intermittently (e.g., every few hours or every day). The risk factors can be iteratively determined, averaged or trended over time and the results used in later processing. In some embodiments, the evaluation of one or more risk factors may be triggered by another event, such as a trended error in BG (e.g., from outlier detection) meeting one or more criteria.

In some embodiments, certain risks factors are evaluated more often or less often than the other of the risk factors. In some embodiments, when one or more risk factors meet one or more predetermined criteria, any of a) the process for dynamically and intelligently determining or detecting the end of life of a sensor (700), b) the process (710) of evaluating one or more other risk factors or c) the process (720) for determining an end of life status may be initiated responsive thereto.

In some embodiments, detection of end of life may be achieved using a combination of methods that each individually detect of end of life signatures or risk factors. The combination of methods or signatures may result in improved specificity (e.g., low false positives). It should be appreciated that the end of life determination methods or algorithms can use a combination of the risk factors in determining end of life.

In some embodiments, suitable risk factors may be selected from the list including, but not limited to: the number of days the sensor has been in use (e.g., implanted); sensor sensitivity or whether there has been a decrease in signal sensitivity (e.g., change in amplitude and/or variability of the sensitivity of the sensor compared to one or more predetermined criteria), including magnitude and history; noise analysis (e.g., EOL noise factors (skewness, spikiness, & rotations)), duration, magnitude and history, spectral content analysis, pattern recognition); oxygen (e.g., concentration and/or whether there is a predetermined oxygen concentration pattern); glucose patterns (e.g., mean, variability, meal characteristics such as peak-to-peak excursion, expected vs. unexpected behavior such as after a meal if glucose is not rising as expected); error between reference BG values and EGV sensor values, including direction of error (whether BG or EGV is reading higher as compared to the other); and measure of linearity of the sensor (or the lack thereof). Sensor linearity refers to a consistency of the sensor's sensitivity over a particular range of measurement (e.g., 40-400 mg/dL for glucose sensors). For example, when the sensor signal is reading low with low BG and high with high BG, linearity may be assumed vs. when the sensor signal is reading low with low BG but not reading high with high BG (not changing or increasing beyond a certain BG value), where non-linearity may be assumed (based on error between reference BG values and EGV sensor values).

One risk factor that may be useful in the determination of end of life is the number of days the sensor has been in use (e.g., implanted). The processor module may be configured to determine how many days the sensor has been in use (e.g., implanted). In some embodiments, the number of days the sensor has been in used is determined based in part on using initial calibration data, sensor initialization, operable connection of the sensor with sensor electronics, user entered data, or the like. In some embodiments, the processor module detects sensor restart and uses restart information in the determination of the days since implantation.

In some embodiments, when a certain threshold has been met, e.g., a certain number of days, the particular variable associated with the threshold may be automatically used in the end of life function. For example, if the number of days the sensor has been in use is determined to be at least 4 days, then the number of days the sensor has been in use is automatically used and/or a simple yes/no indicator that the threshold has been met. In some embodiments, if the number of days the sensor has been in use is at least ⅓ of the days the sensor is approved for use, then the number of days the sensor has been in use is automatically used. In other embodiments, if the number of days the sensor has been in use is at least ½, ⅔, or ¾ of the days the sensor is approved for use, or the like, then the number of days the sensor has been is automatically used. In some embodiments, the actual number of days the sensor has been in use is always used in the end of life function. In some embodiments, the end of life function is performed after a predetermined number of days of sensor use.

Additionally or alternatively, time elapsed from insertion may be mapped to an end of life risk factor value (e.g., likelihood of recovery or probability of sensor failure in future) because the longer a sensor has been in use since implantation, the more the sensor-tissue interface changes (bio-fouling) will likely impact sensor function. Translation of end of life risk factors into values will be discussed in greater detail in reference to block 720 and/or FIG. 10. In one example, the end of life risk factor value is mapped to about 1.0 between days 1 and 5 and reduces gradually beyond day 5 reaching to 0.5 at day 8, 0.2 at day 10, and about 0.1 at day 14. Other values and thresholds may be used as may be appreciated by a skilled artisan.

Another risk factor that may be useful in the determination of end of life is sensor sensitivity or whether there has been a decrease in signal sensitivity (e.g., change in amplitude and/or variability of the sensitivity of the sensor compared to one or more predetermined criteria), including magnitude and history. In some embodiments, the processor module may be configured to determine if there has been a drop in signal sensitivity. For example, for some sensors, their sensitivity drifts up or remains relatively flat over most of the life of the sensor, e.g., 3, 5 or 7 days. Towards the end of life, the sensitivity of the sensor to changes in glucose may decrease. This reduction may be recognized as a drop in sensitivity that occurs monotonically over several hours (e.g., 12 hours), either by determining: (a) a change in sensitivity (e.g., m in raw_signal=m*glucose+baseline) or (b) a reduction in sensor raw count signal. For example, the following equation may be used:

If median(raw count over last 12 hours)−median(raw count over last 12-24 hours)<2*standard deviation over the last 12 hours, then the sensor may be nearing end of life.

In some embodiments, other forms of signal descriptive statistics related to signal sensitivity (e.g., median, percentiles, inter-quartile ranges, etc.) may be used to detect end of life. In some embodiments, whether there has been a decrease in signal sensitivity involves a determination that compares a measured signal sensitivity against a predetermined signal sensitivity threshold or profile to determine if the measured signal sensitivity is within an acceptable range. The acceptable range may be based on a priori information, such as from prior in vitro and/or in vivo testing of sensors. In some embodiments the measured signal sensitivity is outside an acceptable range, then the signal sensitivity may automatically be used in the end of life function. In some embodiments, the measured signal sensitivity, a change in sensitivity and/or an indicator of a predetermined sensitivity decline may be used as an input or a variable in the end of life function.

In some embodiments, the sensitivity variable in the end of life function is based on a trend of sensitivity during a particular sensor session (e.g., during the life of the sensor in the host). For example, the determination of whether there has been a decrease in signal sensitivity includes comparing a first measured signal sensitivity at a first time point against a second measured signal sensitivity at a second time point to determine if rate of change in the measured signal sensitivity is within an acceptable range. The acceptable range may be determined by a priori information, such as from prior in vitro and/or in vivo testing of sensors. In one example, a change of greater than 20% over one day may be an indicator of end of life and useful as an input in the end of life detection function. In one example, a rate of acceleration (e.g., rate of drop of sensitivity) of greater than 20% over 12 hours may be an indicator of end of life and useful as an input in the end of life detection algorithm.

In some embodiments, the rate of change of signal sensitivity may be determined based in part on a slow moving average of raw sensor data (e.g., counts). This embodiment takes advantage of the fact that for most patients, the average glucose over time (e.g., a few days or more) remain relatively constant; thus, a change in the average of the sensor data (e.g., uncalibrated (raw or filtered) over time (e.g., 2, 3, 4, 5, 6, 7 days or more) may be interpreted as a change sensitivity of the sensor over time. The results of the slow moving average could be a quantifiable amount and/or simple yes/no indicators of a sensitivity decline that may be useful as one input or variable into the end of life function.

For example, the processor module may use an average of the last x hours (e.g. for 24 hours), a rectangular window averaging or an alpha filter with an exponential forgetting factor to compute the slow moving average to evaluate sensor sensitivity over time. In one example of an alpha filter with exponential forgetting, 'alpha' may be used as follows:

parameter($n$)=parameter($n-1$)*(1−alpha)+ new_info*alpha wherein alpha defines how much of history one wants to remember (how soon to forget). If alpha is 0.01, then in 1/0.01 (i.e., time constant of 100) samples, 63% of previous information is forgotten. Accordingly, if a sampling rate is 12 samples/hr, then 63% of the signal would be forgotten by 100 samples, e.g., ~8 hours. In such example, it would follow that with 3 time parameters or constants, which is about 1 day, only 5% (i.e., 0.37*0.37*0.37=0.05) of signal left from previous day would remain. In the above equation, alpha is a "forgetting factor." Alpha may vary between 0 and 1, and its value dictates how fast old measurements are forgotten by the model. For values of alpha close to 1, the model adapts more quickly to recent measurements. For values of alpha close to 0, the model adapts more slowly to recent measurements. The value of alpha may depend on the elapsed time since the sensor was implanted. The calculation may be recursive or non-recursive.

In some embodiments, sensitivity loss may be indicative of end of life. Sensitivity loss may occur towards the sensor end of life due to physiological wound healing and foreign body mechanisms around the sensor or other mechanisms including reference electrode capacity, enzyme depletion, membrane changes, or the like.

In some embodiments, sensor sensitivity may be computed in using an analysis of uncalibrated sensor data (e.g., raw or filtered). In one example, a slow moving average or median of raw count starts showing negative trends, the sensor may be losing sensitivity. Loss of sensitivity may be computed by calculating a short term (e.g. ~6-8 hours) average (or median) of the sensor output and normalizing it by the expected longer term (48 hours) average sensor sensitivity. If the ratio of short term to long term sensitivity is smaller than 70%, there may be a risk of sensor losing sensitivity. Loss of sensitivity may be translated into an end of life risk factor value, for example a value of about 1 until the ratio is about 70%, reducing to 0.5 at 50% and <0.1 at 25%.

Figure 11A:
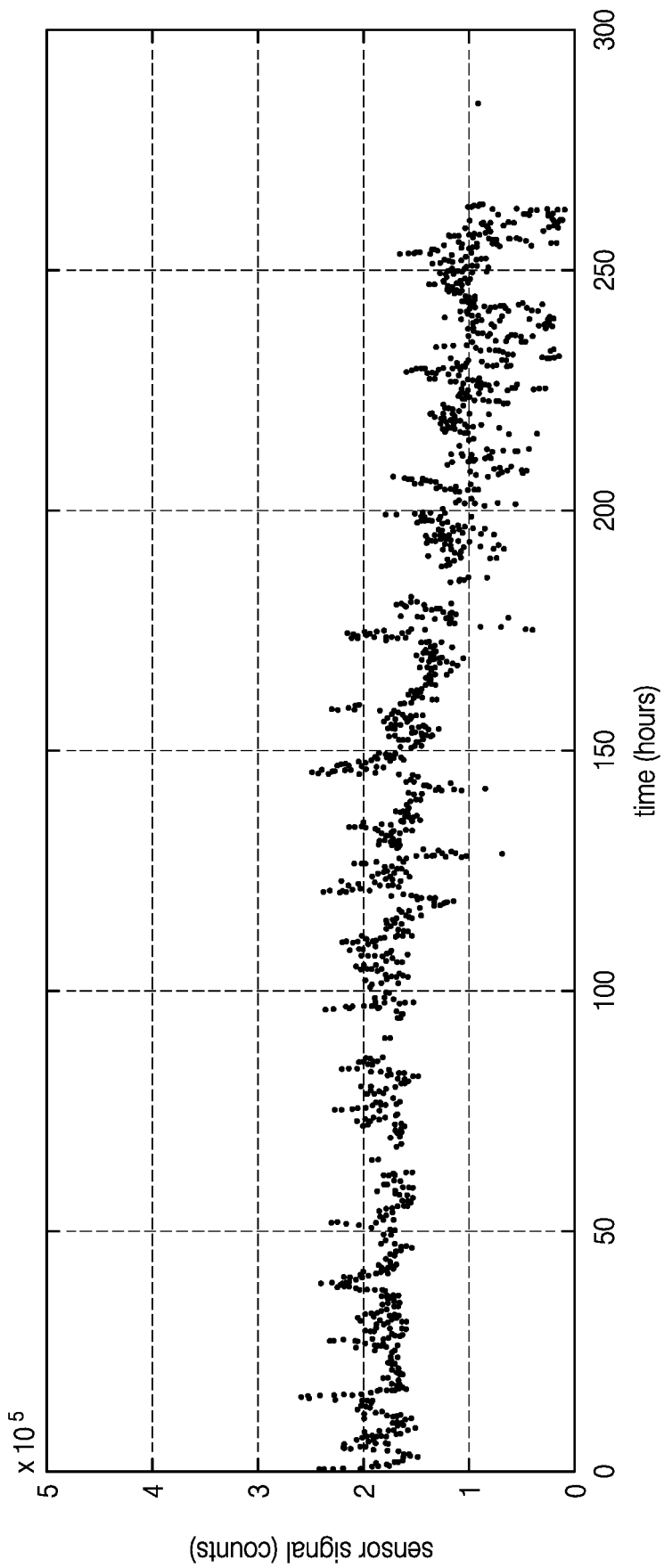
FIG. 11A shows a sensor signal with a loss of sensitivity (downward slope of signal) showing end of life symptoms.

FIG. 11A shows a sensor signal with a loss of sensitivity (downward slope of signal) showing end of life symptoms (x-axis: time in hours, y-axis: sensor signal in counts). From the figure, it can be seen that at about hour 170 (day 8), the sensor signal became significantly noisy with large downward spikes and gradually decreasing amplitude over the next several hours to days due to loss of sensitivity. The end of life detection algorithm identified these two risk factors. For loss of sensitivity, the algorithm first computed a maximum value of count output by the sensor over the last few days and used this max value as the final steady state sensitivity of the sensor. The algorithm compared then calculated the short term (average of last 12 hours) average count. When the short term average counts were lower than the normal variation during 8 hours (i.e., 2 times standard deviation in last 8 hours), then the algorithm flagged the sensor as at risk for end of life. The end of life risk factor value was computed as follows: If short term average is within 80% of long term average, end of life risk factor value was 1. As the ratio of short to long term went below 0.6, the end of life risk factor value was less than 0.5 and reached close to 0.1 if the ratio goes below 0.4. Alternative computations for risk of end of life related to sensitivity may use external references such as glucose finger stick readings. In either case, specific estimated sensitivity loss may be transformed into end of life risk factor values using functions described elsewhere herein.

In some embodiments, sensor sensitivity may be computed by comparing sensor data (e.g., calibrated sensor data) with reference blood glucose (BG). For example, calibration algorithms adjust the glucose estimates based on the systematic bias between sensor and a reference BG. End of life algorithms may use this bias, called error at calibration or downward drift, to quantify or qualify end of life symptoms. The error at calibration may be normalized to account for irregular calibration times and smoothed to give more weight to recent data (e.g., moving average or exponential smoothing). In some embodiments, end of life risk factor value is determined based on the resulting smoothed error at calibration. In such embodiments, end of life risk factor value is 1 for all values of error at calibration>−0.3, and reduces to 0.5 at error at calibration=−0.4, and to <0.1 for error at calibration=−0.6.

Another risk factor that may be useful in the determination of end of life is end of life (EOL) noise based on a noise analysis e.g., EOL noise factor (skewness, spikiness, & rotations), duration, magnitude and history, spectral content analysis, pattern recognition, etc. In some embodiments, the processor module may be configured to evaluate the noise (e.g., amplitude, duration and/or pattern) to determine if there is a predetermined noise pattern indicative of EOL. For example, typical sensor end of life signature may include an increase in spike activity, which can be detected using various methods of spike detection (e.g., by computing the mean rate of negative change).

Figure 15:
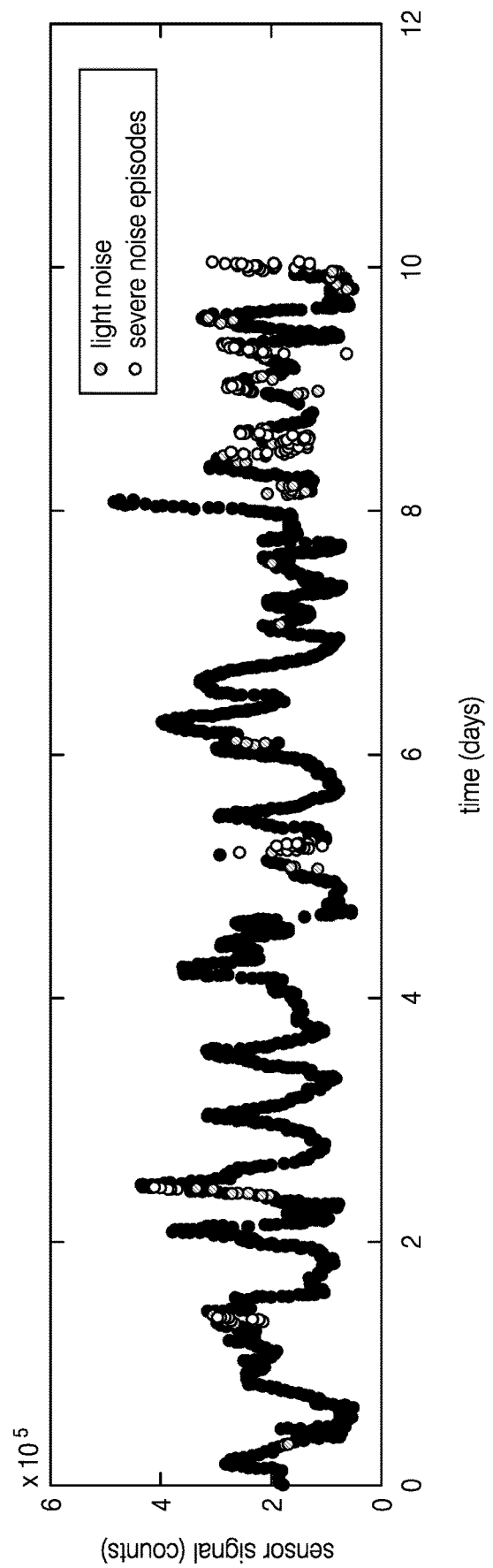
FIG. 15 illustrates a diagram showing noise duration associated with end of life in accordance with an embodiment.

In some embodiments, the duration of the noise may be indicative of end of life. FIG. 15 illustrates a diagram showing noise duration associated with end of life. Some noise detection algorithms that may be useful are described in further detail in U.S. Pat. No. 8,260,393, incorporated herein by reference in its entirety. In some embodiments, the inputs to the calculation of noise duration risk factor metric is the noise categorization of sensor data. For example, each raw sensor count may be categorized as clean, light noise, medium noise or severe noise based on the relative magnitude of sensor and filtered sensor counts and their derivatives. The EOL algorithm described in block 710 may use this information to translate severe noise duration (e.g., amount of sensor data that are in severe noise state) into a metric that reflects end of life risk. An assumption behind calculation of this metric is that sensor end of life manifests as episodes if continuous noise is detected rather than intermittent noise of a few samples. Thus, end of life algorithm may penalize the longer duration noise more, such as shown in FIG. 15. Thus, at each sample time, total duration of noise up to the point is used to calculate the end of life risk factor value at that point.

In some embodiments, whether there is a predetermined end of life signature (noise pattern) involves a determination that includes evaluating the measured signal using pattern recognition algorithms to determine identify predetermined an end of life signature in the sensor signal. For example, by comparing the measured sensor signal against a noise pattern characteristic of end of noise to determine if the recorded noise pattern is similar to the predicted noise pattern.

In other embodiments, the determination of whether there is a predetermined noise pattern (end of life signature) includes comparing the measure signal against a predetermined noise pattern to determine if the recorded noise pattern is similar to the predetermined noise pattern. For example, the predetermined noise pattern may include a series of specific negative spikes in a short time frame. The predetermined noise pattern may include an increase in spike activity for a given time frame.

In one embodiment, threshold detection for rate of change may be used to detect upward or downward spikes. Spikes may be detected by as may be appreciated by one skilled in the art. For example, point to point difference and thresholding, sharpness filters, etc. For example, an algorithm or function may output a +1 for an upward spike and a −1 for a downward spike. Using this spike data time series, one may use either upward spike (positive) spike detection algorithms or downward (negative) spike detection algorithms or total spike detection (e.g., positive or negative spike time series) algorithms.

In some embodiments, end of life detection using these spike detection functions may be achieved using a negative threshold on the moving average of spike time series (e.g., 2 times negative spikes than positive) or a threshold (e.g. 3 or 4) on total spike activity showing a 3 to 4 times increase in total spike activity. Other forms of spike detection such as least squares acceleration filters may be employed. In some embodiments, an end of life risk factor value may be determined to be 1 for a value of a spike metric <1, and reduced to 0.5 for a spike metric >2, and to <0.1 for spike metric >5, and so on.

Figure 11B:
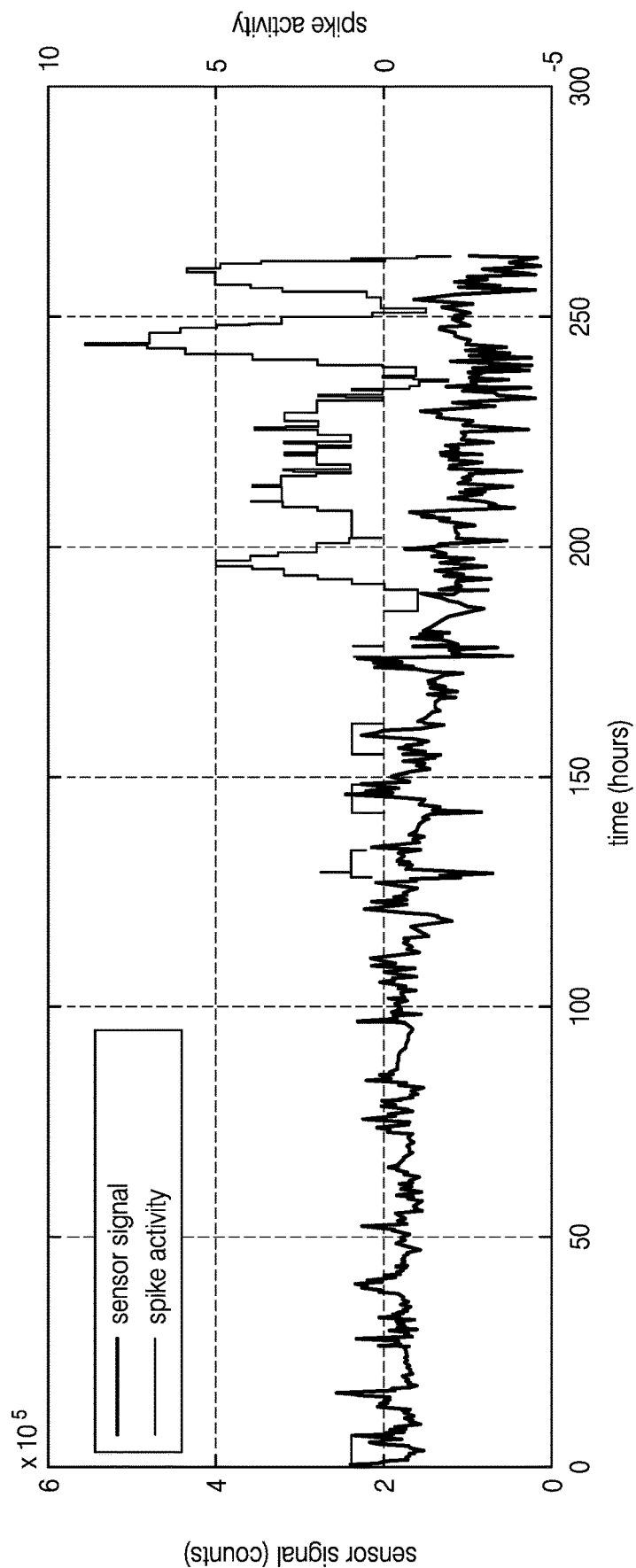
FIG. 11B illustrates the use of a spike detector to detect an increase in downward spikes in a signal produced by a sensor, which is a specific risk factor for end of life.

FIG. 11B illustrates the use of a spike detector to detect an increase in downward spikes in a signal produced by a sensor, which is a specific risk factor for end of life (x-axis, time in hours, left y-axis: sensor signal in counts, right y-axis: output of spike detection filter). In some embodiments, noise occurring during sensor end of life may show large (e.g., greater than about 30% drop in amplitude) downward spikes (spikes that have overall negative change from average) in the midst of some random noise. In order to detect this type of end of life noise, the spike detection filter first identified positive and negative spikes as those that have a point to point change in signal of more than 33%. Then negative spikes were identified by looking at the average signal within the last 30 min (6 samples) when compared to the last 12 samples. The output of these steps was a signal that is +1 for a negative spike and zero elsewhere. The algorithm then computed a moving average of 2 hours of this signal (zeros and ones) to obtain the final output shown. A value of greater than 2 is considered to be indicative of risk for end of life.

In addition to or alternatively, high frequency activity or patterns may be used in end of life detection. For example, end of life signature patterns may show a significant increase in high frequency activity when a power spectral density (PSD) or a Fast Fourier Transform (FFT) is performed on the sensor data. Normal glucose signal has very low frequencies (e.g., 0 and 1.8 mHz). Consequently, a high pass filter or a band pass filter may be used to detect the end of life pattern associated with high frequency activity.

Figure 12A:
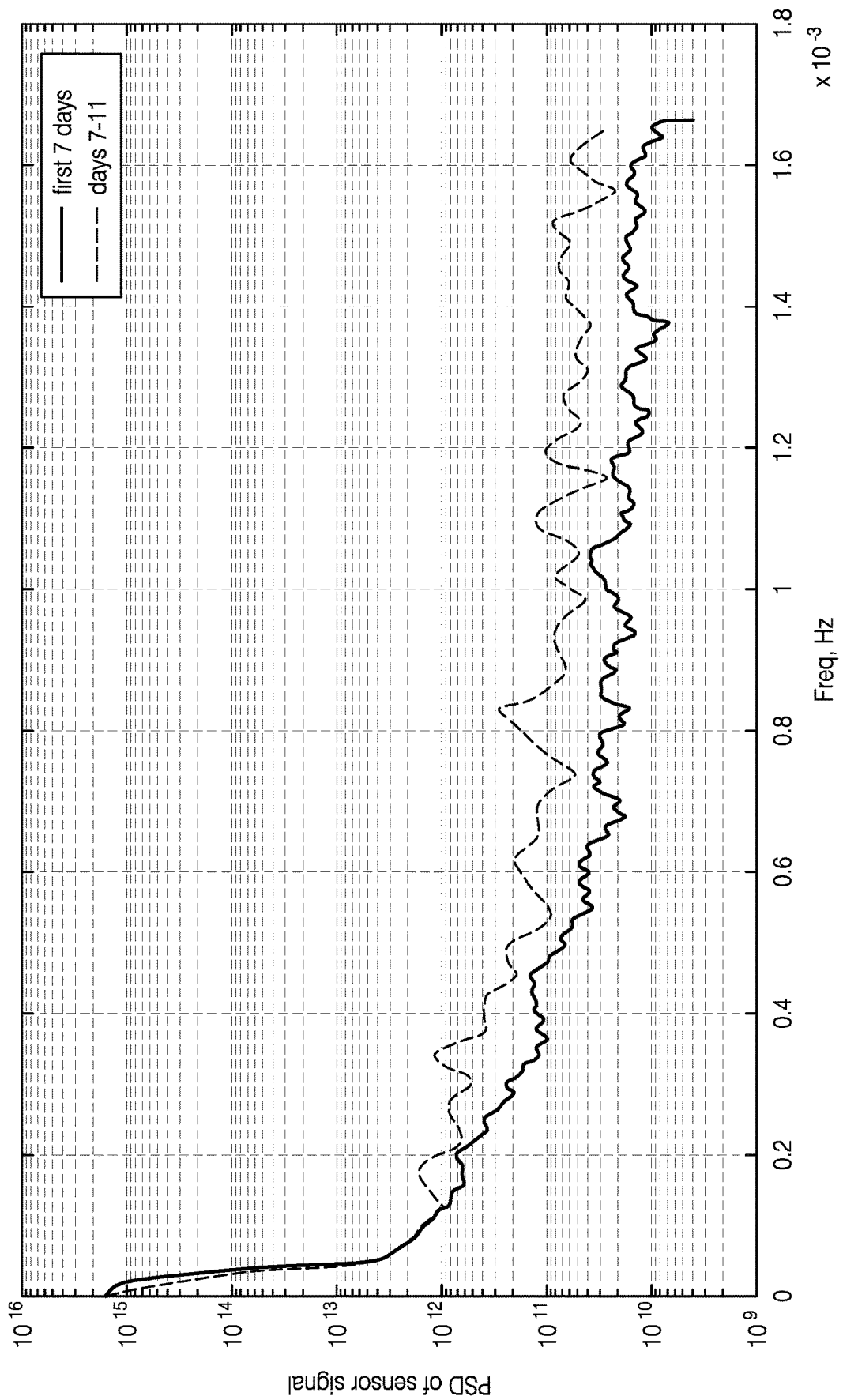
FIG. 12A shows the power spectral density (PSD) of the sensor signal shown in 11A illustrating end of life symptoms.
Figure 12B:
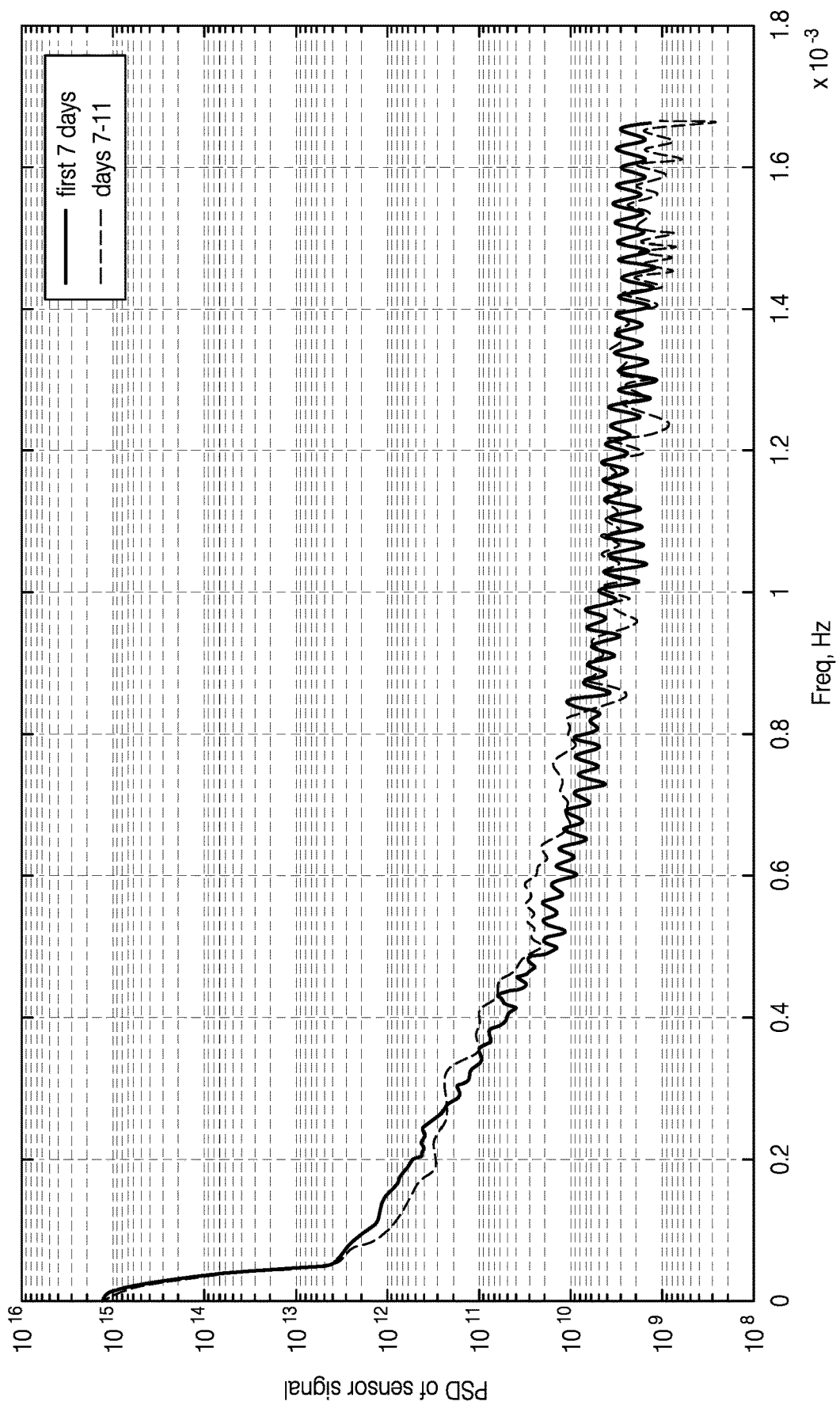
FIG. 12B shows the same type of graph as 12A, but with from a sensor signal that did not exhibit end of life symptoms.

FIG. 12A shows the power spectral density (PSD) of the sensor signal shown in 11A illustrating end of life symptoms. PSD is the energy within each discrete frequency of the signal and was calculated using Matlab pwelch function. Other standard functions implementing FFT may also be used. The energy content of the signal is calculated over a window of about 5 hours, and exceeded the expected energy by more than 10 times (i.e., freq. >0.2 mHz), resulting in the algorithm identifying a risk for end of life. The solid trace shows the PSD of the first 7 days of the signal when no end of life symptoms were seen and the dashed trace is the PSD when end of life symptoms were seen. FIG. 12B shows the same type of graph as 12A, but with from a sensor signal that did not exhibit end of life symptoms. The sensor performed well, as indicated by no change in energy content in higher frequencies even after seven days. In these examples, the PSD of the sensor signal was monitored continuously. In FIG. 12A, the measured PSD increased on Days 7-11 as compare to the expected PSD (measured from the First 7 days), showing an end of life risk factor; while in FIG. 12B, the measured PSD (days 7-11) tracked more closely to the expected PSD (from first 7 days) showing no significant risk of end of life. Expected PSD may computed using a priori sensor knowledge (e.g., by using sensor data from the first few days of sensor life of the same or of a different patient or sensor session). In some embodiments, an end of life risk factor value is 1 for sensors whose short term PSD (at specific frequencies above 0.2 mHz) is about 1-2 times the expected PSD, reduces to about 0.5 if short term PSD is >5 times the long term and reduces further to <0.1 if short term PSD is close to 10 times expected PSD.

In some embodiments, a slow changing long-time scale average signal may be used to normalize the data to enhance the reliability of detection methods, e.g., signal sensitivity or noise pattern. For example, by using the following definitions:

> Long_time_scale=long time (1-2 day) moving average or filtered raw glucose data Signature=short term (~4-6 hrs) filtered (any including spike detection) data Normalized_Signal=Signature/Long_time_scale Thresholds for normalized signal and duration constraints may be applied to detect end of life signatures. Consequently, end of life may be detected if:

> Normalized Signal>Threshold for greater than certain Duration.

In some embodiments, the threshold and duration may be optimized to achieve specific sensitivity and specificity. Alternatively, having a short duration constraint may be used to detect oxygen noise instead of end of life.

Figure 10:
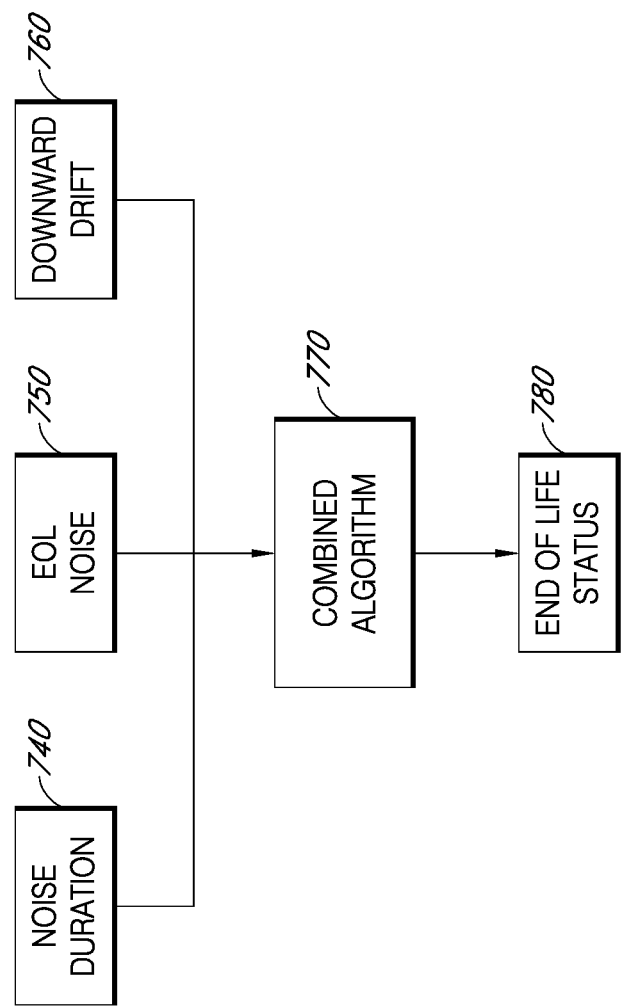
FIG. 10 illustrates a flowchart showing example inputs and outputs for the flowchart of FIG. 9.

With reference to FIGS. 9 and 10, any noise detection algorithm(s) may be used to quantify the duration of noise (740) of a certain amplitude, for example, as described in more detail in U.S. Pat. No. 8,260,393, which is incorporated herein by reference in its entirety. This noise analysis may also be used to determine whether to display or not display glucose to a user. For severe noise (above a predetermined level), the algorithm further may process the signal to determine the end of life risk factor value base on this noise.

In some examples, EOL noise (block 750) may be determined to be sensor end of life specific based on various algorithms that evaluate known end of life failure modes identifiable on the signal. It may have large (>30% point to point drop) downward spikes, negatively skewed over the duration of an episode, with intermittent rapid rotations or oscillations, e.g., multiple peaks and valleys or number of derivative sign changes. Noise discrimination can use these features to identify if a sensor shows end of life symptoms and depending on the magnitude and duration, can calculate the end of life risk factor value from an episode, which may also be termed the noise factor.

Another risk factor that may be useful in the determination of end of life is oxygen (e.g., concentration and/or whether there is a predetermined oxygen concentration pattern). For example, in some embodiments, the processor module may be configured to determine if there is predetermined oxygen concentration and/or trend or pattern associated with the oxygen concentration. Any oxygen sensor useful for quantifying an oxygen concentration may be useful here, separate from or integral with the sensor. In an electrochemical sensor that includes a potentiostat, pulsed amperometric detection can be employed to determine an oxygen measurement. Pulsed amperometric detection includes switching, cycling, or pulsing the voltage of the working electrode (or reference electrode) in an electrochemical system, for example between a positive voltage (e.g., +0.6 for detecting glucose) and a negative voltage (e.g., −0.6 for detecting oxygen). In some embodiments, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which could be ground or 0.0V, which causes the reference to shift, reducing the bias voltage such as described in more detail below. In other words, a common result of ischemia will be seen as a drop off in sensor current as a function of glucose concentration (e.g., lower sensitivity). This happens because the working electrode no longer oxidizes all of the $H_2O_2$ arriving at its surface because of the reduced bias.

In some embodiments, a non-enzyme electrode or sensor may be used as an oxygen sensor. In an exemplary dual working electrode sensor, having enzyme and no-enzyme working electrodes, the non-enzyme electrode may be used as an oxygen sensor by changing the bias potential from a positive value (e.g., 600 mV-800 mV) to a negative value (e.g., negative 600 mV-800 mV). At this potential, dissolved oxygen is reduced and gives rise to a negative current through the non-enzyme electrode. In some embodiments, by switching the bias potential on the non-enzyme electrode between the indicated positive and negative biases, a bi-functional electrode results. When a positive bias is applied, the current may be related to baseline and when a negative bias is applied, the current may be related to the local oxygen concentration.

It is known that glucose oxidase based sensors are limited by the amount of oxygen present. When the oxygen level reduces below a threshold value, the enzyme electrode current drops ("oxygen starvation") while the glucose concentration remains constant. This oxygen starvation may result in reduced accuracy, as lower than actual glucose levels may be reported. Oxygen starvation can occur late in sensor life, such as when the sensor is encapsulated in the subcutaneous environment. Consequently, being able to measure oxygen allows the detection of this encapsulation and end of life for the sensor.

In some embodiments, whether there is a predetermined oxygen concentration pattern involves a determination that includes reviewing the oxygen concentration pattern to see if the oxygen concentration is appropriate. For example, an oxygen concentration pattern that shows reduction in oxygen availability over time may be indicative of end of life of the sensor.

Another risk factor that may be useful in the determination of end of life is glucose pattern (e.g., mean, variability, meal characteristics such as peak-to-peak excursion, expected vs. unexpected behavior such as after a meal if glucose is not rising as expected).

Still another risk factor that may be useful in the determination of end of life is error between reference BG values and corresponding calibrated sensor data (estimated glucose value, or EGV), including direction of error (e.g., whether BG or EGV is reading higher as compared to the other) and/or utilizing flagged outliers, as described in more detail elsewhere herein. In some embodiments, the processor module may be utilized to identify discrepancies between reference values (e.g., BG) and sensor values (e.g., EGV). For example, as discussed above in the outlier detection, when there is a large difference in the reference values and sensor values, something is likely not working correctly. In certain embodiments, a large discrepancy between the reference values and sensor values may indicate end of sensor life. While not wishing to be bound to any particular theory, this is believed because the sensor is reading either higher or lower than it should. In some embodiments, the direction of the error, for example whether the BG is higher or lower than the EGV is used as an end of life indicator as described also with reference to block 710. Still another risk factor that may be useful in the determination of end of life is a measure of linearity of the sensor (or the lack thereof). As described above, sensor linearity refers to a consistency of the sensor's sensitivity over a particular range of measurement (e.g., 40-400 mg/dL for glucose sensors).

In some embodiments, the processor module is configured to evaluate the various risk factors to provide end of life risk factor values, which may include simple binary (yes/no) indicators, likelihood or probability scores (e.g., relatively scaled or percentages) and/or actual numbers (e.g., outputs of the various tests). The risk factor values may be scaled if the weights used in the algorithm are modified.

Figure 13A:
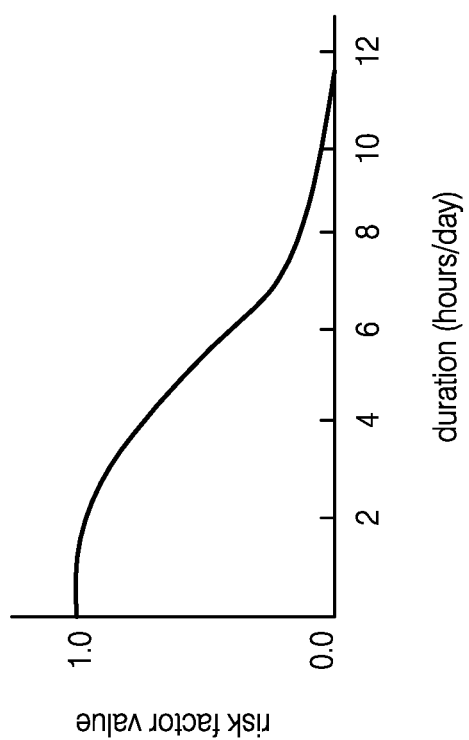
FIG. 13A illustrates a translation function that maps a noise duration to an end of life risk factor value in one embodiment.
Figure 13B:
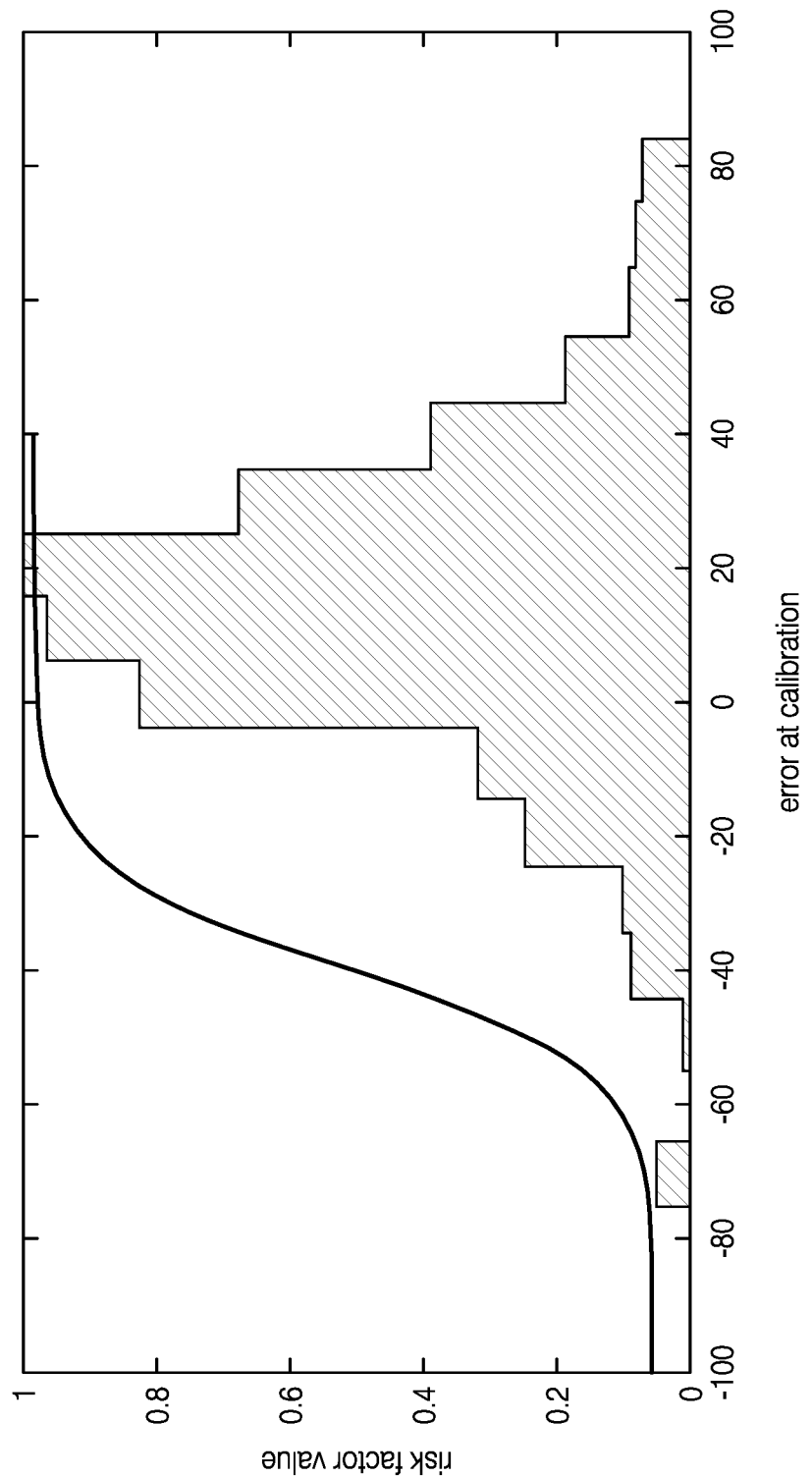
FIG. 13B illustrates a translation function that maps the error at calibration to an end of life risk factor value in one embodiment.

In some embodiments, the processor module is configured to run probability functions to determine a probability of end of life and/or a likelihood of recovery for one or more of the plurality of end of life risk factors. In some embodiments, risk factors are mapped to a score (e.g., from 0 to 1) based on one or more parameters. The score may be mapped by functions, such as illustrated in FIGS. 13A and 13B, which translate a particular risk factor or set of risk factors to an end of life risk factor value, indicating for example, a possibility of the sensor to recover from a particular risk factor from end of life. Other methods of translating risk factor outputs into end of life risk factor values may be used as is appreciated by a skilled artisan, such as by using one or more criteria, algorithms, functions or equations.

In some embodiments, risk factors are fuzzified using pre-determined membership functions in order to quantify their propensity to indicate end of life. As used herein, a membership function defines the degrees to which a condition is satisfied, or a degree to which a value belongs to a fuzzy set defined by that function. In binary logic, a number would either satisfy a condition fully or not at all; in fuzzy logic, a number can satisfy a condition to a certain degree described by a membership function.

As an example of a binary indicator function, a noise level is compared to a hard threshold, such as "5"; any value below 5 (such as 4.9) is treated as being noise-free and any value above 5 (such as 5.1) is treated as having an unacceptable level of noise. As an example of a fuzzy membership function, a sigmoidal shape may be used to define a smooth transition in the evaluation of the noise levels. The inflection point of the curve is set at 5, so there is no discontinuity at that point. Thus, the same values of noise (4.9 and 5.1) as above are now treated very similarly. Fuzzification is the determination of the degree to which a value belongs to a fuzzy set defined by a particular membership function.

In some embodiments, each of the plurality of risk factors is partially indicative of the end of life of the sensor if each variable is determined to meet a threshold. In some embodiments, if at least two of the plurality of risk factors are determined to meet a threshold, then the combination of the at least two risk factors is indicative of the end of life of the sensor.

At block 720, the processor module is configured to determine an end of life status. In one embodiment, a likelihood or probability analysis may be used to determine an end of life status of the sensor. The outputs of the risk factors evaluated at block 710 become inputs into the end of life determination process (block 720). As described in more detail elsewhere herein, the outputs of the risk factors of 710 may be mapped to end of life risk factor values, for example values from 0 to 1, probability or likelihood scores, actual values (outputs from the risk factor evaluation(s)), and/or the like. The end of life risk factor values then become inputs into the end of life determination function, whereby the risk factors may be weighted or otherwise processed by the processor module using a probability analysis, decision matrix, various subroutines or the like, to determine an actual end of life indicator, a probability (or likelihood) of end of life, a predicted time to end of life, or the like. Probability functions, decision functions, various subroutines, or the like may be implemented as the end of life determination function as is appreciated by one skilled in the art.

In one embodiment, decision fusion may be used as the function through which the various inputs are processed (e.g. into block 720). Decision fusion may provide a Fused Bayesian likelihood estimate based on sensitivity and specificity of individual detector algorithms associated with each input or variable. Suitable risk factors are measured, as described in more detail above with reference to block 710, and fused together to determine whether or not a sensor has reached end of life (EOL). A decision can be made for "yes" EOL or "no" EOL based on each individual risk factor. For example, if sensor sensitivity has decreased by more than Δm over some amount of time Δt then "yes" EOL otherwise "no", or if the sensor has had severe noise (above a predetermined threshold level) for more than 12 hours of the last 24 hours then "yes" EOL, otherwise "no".

The individual decisions can be combined into a single Bayesian likelihood value that can be used to make the best final decision about EOL, using the sensitivity and specificity of each variable in detecting EOL. First, each decision is converted to a likelihood value using the following equation:

$$\lambda(d) = \frac{P(d|H_1)}{P(d|H_0)}$$

where d is a binary decision of 0 or 1 (no or yes), $H_1$ is the case that EOL is present, $H_0$ is the case that EOL is not, and P( ) is the probability function. In practice, this means for a "yes" decision $\pi$=sensitivity/(1−specificity), and for a "no" decision $\lambda$=(1−sensitivity)/specificity. For an individual variable test with high sensitivity and specificity, $\lambda$ will be very high for a decision of 1 and very small for a decision of 0.

In some embodiments, the individual likelihood values are multiplied together for a final fused likelihood value that takes into account the ability of each individual variable to separate EOL from non-EOL. Thus, more sensitive and specific tests will be given greater weight in the final decision. A threshold may be determined empirically for the final fused likelihood values to achieve the best separation of EOL and non-EOL.

In some embodiments, linear discriminant analysis (LDA) may be used as the end of life determination function, by taking the input variables and providing an output decision.

In some embodiments, when EOL inputs or variables are fuzzified using pre-determined membership functions, resulting degrees of membership for all data quality metrics are scaled according to pre-determined weights and combined to produce an indicator of the overall quality of the computed glucose value. The weights may be applicable to every metric and may show how indicative a metric is of end of life. These embodiments may use several fuzzy logic concepts such as membership functions and fuzzification, as described above, to determine the degree of severity of each data quality metric. It should be understood that the fuzzification and membership functions can be applied to the processor module. The result of the end of life detection (block 720) may be a confidence indicator that determines a likelihood of end of life beyond a simple pass/fail criterion.

In some embodiments, the processing moves immediately to block 730 to provide an output related to (e.g., associated with and/or responsive to) the end of life status determined at 720 (e.g., alert the user that sensor is at its end of life or is predicted to end at a certain time point). In some embodiments, end of life status may be determined based on likelihood of a sensor not recovering from an event rather than occurrence of an event; the likelihood of a sensor not recovering may be defined as the state when a sensor is likely to be no longer accurate or has long episodes of noise (e.g., based on risk factor evaluation(s)). The end of life indicator may also indicate a possibility of recovery (e.g., when the episode may be transient rather than terminal). In some embodiments, the processor module is configured to determine a likelihood of recovery and/or monitor the sensor or sensor data over the next x hours to determine whether the sensor may recover from the end of life symptoms (e.g., the likelihood of sensor providing accurate data to user in next 24 hours). In some embodiments, the sensor will only be determined to be at end of life if a high probability of sensor not tracking glucose in the future (e.g., 24 hours) or not showing glucose at all for several hours (e.g., 12 hours) is determined (e.g., inaccuracy may be determined by a comparison of EGV with reference BG using a standard (e.g., within 20% or 20 mg/dL)).

Integral to or after block 720, the processor may optionally be configured to monitor the risk factors (e.g., for example more frequently after end of life indicator determines a likelihood of end of life) to determine whether it is more than likely that the sensor will not recover from the end of life determination. Functions or algorithms suitable for determining whether a sensor will recover from EOL may be selected from those known by one of skill in the art. For example, determining whether a sensor will recover may be a 0 to 1 scaling based on an evaluation of one or more risk factors.

In some embodiments, the processor may be configured to determine, based on recent history, the likelihood of a sensor to recover from the end of life determination. For example, the EOL determination function may determine the end of life status is more than likely if there is a high probability that the sensor will not track glucose in the future or that the sensor is not detecting glucose at all for extended durations. Extended durations may include time periods exceeding 12 hours. In some embodiments, the processor module is configured to suspend display of sensor data during verification or determination of a likelihood of recovery, after which the processor module may be configured to either re-allow display of sensor data if it is determined that the sensor has recovered from the end of life symptoms. If, however, it is determined that more than likely the sensor will not recover from the end of life symptoms, the processing moves to block 730.

At block 730, the processor module may be configured to provide an output related to the end of life status of the sensor. For example, a message related to the end of life status may be provided to a user (e.g., via a display). In some embodiments, the message to the user is provided on the sensor display itself. In other embodiments, the message is provided to a remote device, such as a laptop or mobile phone (e.g., smartphone). In some embodiments, end of life status (e.g., or information related thereto) is transmitted to an insulin delivery device, for example, closed-loop algorithm that controls an insulin pump. For example, the end of life status or score may be compared to one or more criteria that dictates the processing or output responsive thereto.

It should be appreciated that a goal of end of life detection is to reduce the risk to performance occurring after the sensor has been in use for many days. In some embodiments, the user may be notified. For example, if end of life shut off occurs after day 5 (e.g., of a 7-day sensor), the user may be notified twice. For example, an alarm may be triggered immediately after BG entry.

In some embodiments, advantages of detecting end of life for a sensor includes: recognition of sensor failure would enable replacement of the sensor so that accuracy of glucose estimation is not significantly impacted, end of life pattern recognition may be used in preventing closed-loop systems (e.g., artificial pancreas) from incorrect dosing, and extended use of sensor beyond the designed life of sensor may be recognized. As explained above, replacement of sensor so that accuracy of glucose estimation is not significantly impacted is desirable because it allows the user to rely on sensor readings with confidence. Similarly, recognition of extended use of sensor is desirable because it allows the sensor system to adjust the expectations or glucose estimation according to known contributors (e.g., drift, oxygen reduction, etc.) or to advise the user that they are not using the sensor in accordance with e.g., FDA regulations, or to prompt the user to change the sensor (e.g., by providing a message to the user), or to deactivate/disable the sensor, etc., as described in more detail below.

In some embodiments, intermittent signs of end of life may be used to turn on advanced signal filtering techniques. Such filtering techniques are described, for example, as described in more detail in U.S. Pat. No. 8,260,393, which is incorporated herein by reference in its entirety.

In some embodiments, a message provided to the user related to the end of life status includes instructions to change the sensor if the end of life is determined to occur within a predetermined time frame. The predetermined time frame may be based on the predicted time to end of life, based on a predetermined time period of about 1, 2, 3, 4 hours or more, or the like. In other embodiments, a message related to the end of life status includes a warning that the sensor will shut down in a predetermined time frame if the end of life is determined to have occurred. The predetermined time frame may be immediately or within a few minutes or a few hours.

In other embodiments, the output provided in block 730 may include an instruction, command, or set of instructions to suspend what is being shown on the display (e.g., to the user or host) to avoid showing inaccurate data on the display based on the end of life score or status as compared to a criterion, for example.

In still other embodiments, the output provided in block 730 may include an instruction, command, or set of instructions to shut the sensor down, disable display of real-time sensor data, instruction a user to remove the sensor, or the like, based on the end of life score or status as compared to a criterion, for example. In some embodiments, the instruction may shut off the display and/or shut off the monitor itself. Advantageously, the system is configured to not allow the user to restart the session until a new sensor insertion has been verified.

Referring now to FIG. 10, a flowchart showing example processes associated with the flowchart of FIG. 9 is presented. In some embodiments, the goal of the end of life (EOL) algorithm is to assess a sensor's ability to be accurate and reliable in the future. In this exemplary embodiment, the algorithm monitors noise in sensor data and offset from a BG (error at calibration), translates them into risk factor values and determines the end of life status from current condition state (e.g., noise or large error state).

As illustrated in FIG. 10, inputs to the algorithm may include: duration of noise (740), EOL noise (750) and a downward drift of sensor sensitivity (760) determined based on analysis of error at calibration. These inputs can be iteratively determined or trended over time and the results used in the combined algorithm of block 770. In this example, outputs of for each of the risk factor evaluations may be translated into end of life risk factor values based on current condition or state (e.g., values between 0 and 1), which are fed into combined algorithm of block 770.

As explained in detail above, there are multiple risk factors associated with end of life, including for example: (1) Day of sensor life, e.g., time from insertion, (2) Noise amplitude and duration, (3) Noise type, and (4) Sensitivity Loss. Described herein are how these risk factors may be quantified and likelihood of sensor recovery from these conditions computed. It should be appreciated that the risk factors identified in blocks 740, 750, and 760 may all be evaluated in block 710 of FIG. 9.

In this example, the end of life algorithm has been selectively turned on at a predetermined time (e.g., day 5 after implant), rather than the time since implant being used as an input into the end of life determination algorithm (770). However, the time since implant could further enhance the ability of the end of life algorithm to accurately determine end of life since the longer the sensor is implanted, the more likely the sensor will reach end of life.

In this example, a noise detection algorithm, as described in more detail in U.S. Pat. No. 8,260,393, which is incorporated herein by reference, is used to quantify the sensor data as clean or noisy (light, medium or severe) based on the amplitude of noise and the difference between raw sensor and filtered sensor signal. Noise duration (740) is determined based on the length of noise of a certain severity. When noise episodes of a certain severity (predetermined level of noise) of longer than 2 hours occur, the likelihood of recovery is impacted. FIG. 13A illustrates a translation function that maps a noise duration value to an end of life risk factor value (e.g., from 0 to 1) in one embodiment. Translation functions may be in the form of a function that associates a likelihood of recovery with a duration noise, or may use other mapping techniques, such as look up tables, various subroutines, and/or the like. Although some sensors experience episodes of noise, episodes lasting less than 2 hours of continuous noise may not necessarily be indicative of end of sensor life. Thus, in the example illustrated in FIG. 13A, any continuous noise duration below 2 hours may have a very high value (e.g., risk factor value of 1) indicating a high likelihood of recovery from the noise episode. As the duration increases the likelihood of the sensor being normal decreases as shown. At about 5 hours the likelihood of the sensor being normal decreases to about 50% (e.g., 0.5 risk factor value) and at greater than 8 hours, the risk factor value may translate to about 0.1, for example. In some embodiments, the end of life risk factor value is calculated continuously for some period of time, and the resulting risk factor values may be smoothed, for example, for example using exponential forgetting, or the like. Duration may be tracked cumulatively over a sensor session, on a daily basis (e.g., hours/day), consecutively, or the like.

EOL noise (block 750) is sensor end of life specific based and determined based on algorithms that evaluate the various aspects of the sensor signal related to noise: skewness of a short duration (e.g., 2 hours) of noise, average rate of negative change of signal within this episode, and the number of peaks and valleys in the episode (number of rotations), for example. Once these parameters are calculated, a noise factor (e.g., between 0 and 1) is calculated by combining each parameter as may be appreciated by one skilled in the art. The parameters and/or the EOL noise factor may be smoothed, for example using an exponential forgetting factor. The EOL noise factor may be translated to an end of life risk factor value, similar to FIG. 13A, for example, where a noise factor close to zero translates to an end of life risk factor of 1, while a noise factor>0.5 has <0.5 end of life risk factor. These values may be scaled if the weights used in the algorithm are modified.

Sensitivity Loss or Drift (block 760) is determined based on analysis of an error at calibration (or receipt of reference value). In this example, the error at calibration is calculated by taking the difference between calibrated sensor data and time corresponding reference blood glucose data, and dividing the result by the time since the continuous blood glucose monitor was last calibrated, whereby an indication of downward drift in sensitivity may be inferred, wherein calibrated sensor data is based on sensor data that has already been converted using a previous calibration (conversion function). In this example, the error at calibration is normalized and smoothed. In this example, the likelihood of recovery is estimated based on the resulting smoothed error at calibration as illustrated in FIG. 13B, which is a translation function that maps the error at calibration to an end of life risk factor value. FIG. 13B illustrates a translation function that defines a mapping from an error at calibration to a risk factor value. In this example, when the smoothed error at calibration is less than −20%, the risk factor value is high (closer to 1.0). However, when the error at calibration decreases to below −30%, the risk factor value rapidly decreases and reaches about 0.1 when error is below −50%. This error is asymmetrical because sensor sensitivity tends to decrease as it approaches it end of life.

Figure 13C:
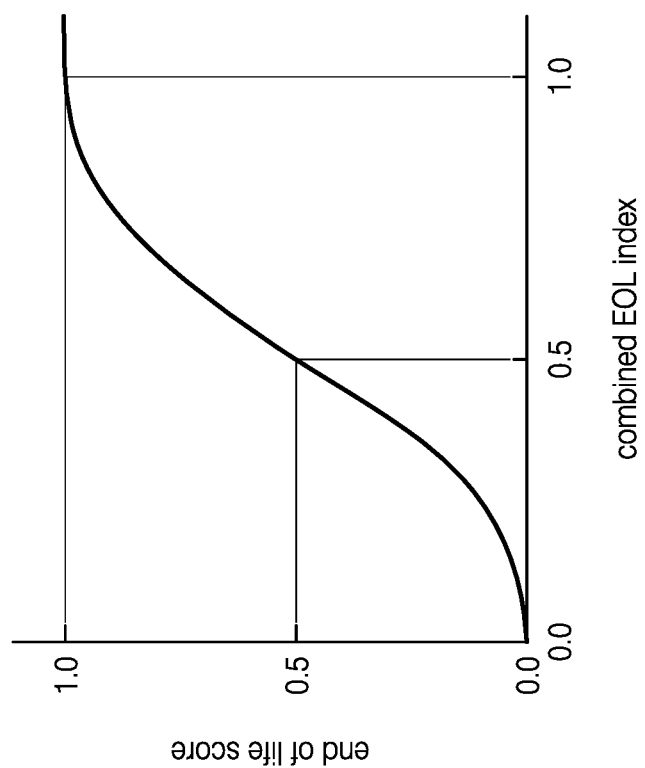
FIG. 13C illustrates a translation function that may be used by the processor module to translate the combined EOL index calculated from the various risk factors to an end of life score and/or end of life status, in one embodiment.

The processor module may then take the risk factor values (740, 750, 760) and combine them into a metric (e.g., a weighted average) or EOL index (block 770), the result of which is then compared against end of life criteria at block 780 to determine an end of life status. FIG. 13C illustrates a translation function that may be used by the processor module to translate the combined EOL index calculated from the various risk factors to an end of life score and/or end of life status, in one embodiment. In this example, after obtaining the various risk factor values, they were summed using a weighted average to obtain the combined EOL index. This risk likelihood index was normalized by the sum of the weights as shown in FIG. 13C. An end of life score close to 1 is indicative of a high likelihood of recovery from the various EOL symptoms (risk factors), but a value close to zero indicates a good possibility or probability that the sensor has reached the end of its life.

It should be appreciated that blocks 770 and 780 may collectively occur in block 720 of FIG. 9. Please note that for all above risk factors, risk factor values may be computed from look up tables or functions developed from a priori knowledge of sensors and their behavior over time. Once these risk factors may be combined into a metric (e.g., a weighted average) or EOL index (block 770), using a suitable algorithm, which is then used to determine an end of life status of the sensor (e.g., if a sensor is likely to be useful and accurate in the future) at block 780 in FIG. 10. If, for example, the overall weighted average of the EOL Index is close to 1, then the sensor is likely to recover from current condition and is likely to be accurate and useful in the future (e.g., next 24 hours). If the weighted average is <0.5, then the sensor is not likely to be useful in the future. This value may be used to take different actions (e.g., provide different outputs at block 730 of FIG. 9).

In another example of how the various risk factors can be combined to determine sensor end of life; the processor module may begin by determining that it is day 5 and evaluate a plurality of blood glucose entries over time to determine end of life. In accordance with block 710, the processor module evaluates a plurality of blood glucose entries over time and the number of days the sensor has been in use. For example, for a first blood glucose entry (BG1), if the sensor data <<reference data (BG1) by more than a predetermined amount (e.g., outside of a 40% or 40 mg/dL difference), one or more resulting values may be considered by the end of life determination function.

If the end of life criteria is met for BG1, the sensor system may prompt the user for a second blood glucose entry (BG2). If BG2 confirms BG1 is an accurate blood glucose value (e.g., by being a comparable value), then the BG values are considered partially indicative of end of life. One skilled in the art can envision subroutines useful to evaluate differences in BG vs. EGV and map likelihood of recovery thereby.

As described above, the processor also considers the number of days the sensor has been in use. For example, the end of life determination process may only begin after a particular day post implant and only when outlier detection identifies an outlier that meets certain criteria. The number of days the sensor has been in use may be determined or derived by examining the maximum possible sensor value based on calibration history (day 4+). If the maximum sensor value still <<BG1 or BG2, then the number of days the sensor has been in use is considered partially indicative of end of life.

Taking into consideration the BG values and the number of days the sensor has been in use, end of life is determined at block 720, using various subroutines, and the likelihood of recovery is determined or determined to be 0. Thereafter, the sensor system may provide instructions to shut off the sensor, in accordance with block 730.

In some embodiments, certain assumptions may be made with the end of life algorithm. For example, the blood glucose readings may be assumed to be accurate. If there are 2 errant blood glucose readings (e.g., sensor <<BG) such as described above in the outlier detection/culling, then the blood glucose values may be partially indicative of end of life (such as described in the present example).

As yet another example of how the various risk factors can be combined to determine sensor end of life, the processor module evaluates a signal for a trend in noise (e.g., signal spikes) and a trend in sensor sensitivity and provides the risk factors to be processed by end of life function or algorithm. This example is described below.

At block 710, the processor module compares the measured signal against a predetermined noise pattern to determine if the recorded noise pattern is similar to the predetermined noise pattern. For example, the predetermined noise pattern may include a series of specific negative spikes in a short time frame. The predetermined noise pattern may include an increase in spike activity for a given time frame. In the present example, the processor module identifies a 3× increase in signal spikes over the past 24 hours, which is a risk factor indicative of end of life.

Similarly, the processor module evaluates the sensitivity over time and identifies a change in sensor sensitivity of more than 20% decline in 24 hours, or compares to an expected profile, such as described with references to FIGS. 1 and 2, which is a risk factor indicative of end of life. As described above, sensor sensitivity may be determined using e.g., a raw count analysis or a comparison with a reference blood glucose value. At block 720, the end of life function processes the spike trend and sensitivity trend using instructions or conditions to determine whether end of life is, has or will occur, or to determine a likelihood of recovery. If the likelihood of recovery is less than 50%, then the sensor system may provide instructions to shut off the sensor, in accordance with block 730.

Sensor Reuse

In some embodiments, sensor reuse can be detected. This may be achieved using the end of life sensor function and comparing the profile of a used sensor against what the profile of a new sensor should look like. Sensor reuse can be dangerous to the user because the sensor may provide inaccurate data upon which the user may rely.

Figure 14:
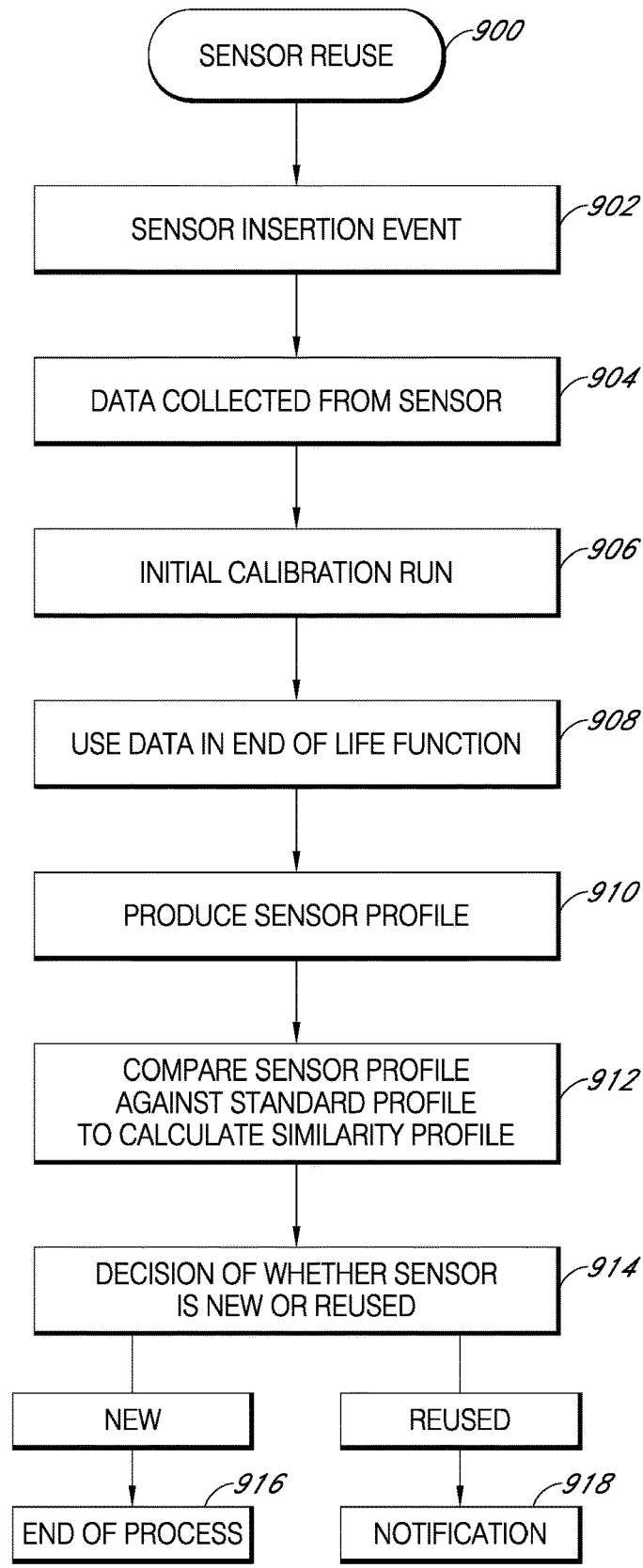
FIG. 14 illustrates a flowchart describing a process for determining sensor reuse associated in accordance with an embodiment.

FIG. 14 is a flowchart of an example process 900 for determining sensor reuse in accordance with an embodiment. At block 902, a sensor insertion event is triggered. An insertion event can be one of any number of possible events that indicate a new sensor has been implanted, such as a user providing input to a sensor system that a new sensor has been implanted, the sensor system detecting electrical connection to a sensor, a predetermined amount of time transpiring since the system prompted a user to use a new sensor, and the like. Next, at step 904, a data point or series of data points are collected from the analyte sensor being used, and an initial calibration is run using the collected data to produce an initial calibration at step 906. Thereafter, in block 908, the data point or series of data points are used as inputs into the end of life sensor function. At block 910, the end of life function produces a sensor profile. The sensor profile may include a graph illustrating noise, sensitivity, etc., as described above with respect to e.g., FIGS. 11-13 and 15. At block 912, the sensor profile from block 910 is compared against a standard sensor profile for a new sensor and a similarity profile is calculated. At step 914, a decision is made whether the calculated similarity profile is indicative of a new sensor or a reused sensor. If the similarity profile indicates a new sensor, example process 900 is ended at block 916. If the similarity profile indicates a reused sensor, a notification may be provided at block 918.

The sensor reuse routine of step 918 can include triggering an audible and/or visual alarm notifying the user of improper sensor reuse. The alarm can also inform the user why sensor reuse may be undesirable, such as potentially providing inaccurate and unreliable sensor readings. The sensor reuse routine 918 can alternatively or additionally cause the sensor system to fully or partially shut down and/or cease display of sensor data on a display of the sensor system.

Exemplary Sensor System Configurations

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

In some embodiments, a sensor system is provided for continuous measurement of an analyte (e.g., glucose) in a host that includes: a continuous analyte sensor configured to continuously measure a concentration of the analyte in the host and sensor electronics physically connected to the continuous analyte sensor during sensor use. In one embodiment, the sensor electronics includes electronics configured to process a data stream associated with an analyte concentration measured by the continuous analyte sensor in order to process the sensor data and generate displayable sensor information that includes raw sensor data, transformed sensor data, and/or any other sensor data, for example. The sensor electronics can include electronics configured to process a data stream associated with an analyte concentration measured by the continuous analyte sensor in order to process the sensor data and generate displayable sensor information that includes raw sensor data, transformed sensor data, and/or any other sensor data, for example. The sensor electronics can include a processor and computer program instructions to implement the processes discussed herein, including the functions specified in the flowchart block or blocks presented herein.

In some embodiments, a receiver, which can also be referred to as a display device, is in communication with the sensor electronics (e.g., via wired or wireless communication). The receiver can be an application-specific hand-held device, or a general purpose device, such as a P.C., smart phone, tablet computer, and the like. In one embodiment, a receiver can be in data communication with the sensor electronics for receiving sensor data, such as raw and/or displayable data, and include a processing module for processing and/or display the received sensor data. The receiver can also and include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver's processing module can include a processor and computer program instructions to implement any of the processes discussed herein, including the functions specified in the flowchart block or blocks presented herein.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Any combination of devices or systems may be used to implement the present methods and processes.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,"desired," or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated. Therefore, the description and examples should not be construed as limiting the scope of the disclosure to the specific embodiments and examples described herein, but rather to also cover all modification and alternatives coming with the true scope and spirit of the disclosure.

What is claimed is:

1. A method for determining an end of life of an analyte sensor, comprising:
    determining a likelihood of recovery based on a plurality of risk factors associated with end of life symptoms of the analyte sensor;
    determining an end of life status of the analyte sensor based on the determining the likelihood of recovery; and
    providing an output related to the end of life status of the analyte sensor,
    wherein the plurality of risk factors includes a change in magnitude of sensor sensitivity, a characterization of noise arising in a signal from the analyte sensor, and a duration of the noise arising in the signal from the analyte sensor.

2. The method of claim 1 wherein the plurality of risk factors further includes a rate of change of sensor sensitivity.

3. The method of claim 2 wherein determining the likelihood of recovery based on the plurality of risk factors comprises evaluating at least one of a direction of rate of change of sensor sensitivity, an amplitude of rate of change of sensor sensitivity, a derivative of rate of change of sensor sensitivity, or a comparison of rate of change of sensor sensitivity to a priori rate of change sensitivity information.

4. The method of claim 1 wherein determining the likelihood of recovery based on the plurality of risk factors comprises evaluating a spectral content of the signal from the analyte sensor or noise patterns by at least one pattern recognition algorithm.

5. The method of claim 1, wherein determining the end of life status comprises determining an end of life score based on the plurality of risk factors.

6. The method of claim 5, wherein determining the end of life status is based on the end of life score.

7. The method of claim 5, wherein determining the end of life score comprises weighting one or more of the plurality of risk factors.

8. The method of claim 1, wherein each of the plurality of risk factors is partially indicative of the end of life of the analyte sensor based on a comparison of the risk factor to one or more criteria.

9. The method of claim 1, wherein determining the end of life status comprises using a probability analysis.

10. The method of claim 1, wherein the output related to the end of life status is displayed on a user interface.

11. The method of claim 1, wherein the output related to the end of life status comprises instructions to change the analyte sensor.

12. The method of claim 1, wherein the output related to the end of life status comprises a data transmission.

13. The method of claim 1, wherein the output related to the end of life status comprises disabling display of sensor data.

14. The method of claim 1, wherein the method is implemented on a computer having a processor and a memory coupled to said processor, wherein at least one of the determining the likelihood of recovery, the determining the end of life status, or the providing the output is performed using the processor.

15. A system for determining an end of life of an analyte sensor, the system comprising sensor electronics configured to be operably connected to the analyte sensor, the sensor electronics configured to:
determine a likelihood of recovery based on a plurality of risk factors associated with end of life symptoms of the analyte sensor;
determine an end of life status of the analyte sensor based on the determination of the likelihood of recovery; and
provide an output related to the end of life status of the analyte sensor,
wherein the plurality of risk factors includes a change in magnitude of sensor sensitivity, a characterization of noise arising in a signal from the analyte sensor, and a duration of the noise arising in the signal from the analyte sensor.

16. The system of claim 15 wherein the plurality of risk factors further includes a rate of change of sensor sensitivity.

17. The system of claim 15 wherein the sensor electronics configured to determine the likelihood of recovery based on the plurality of risk factors comprises evaluating at least one of a direction of rate of change of sensor sensitivity, an amplitude of rate of change of sensor sensitivity, a derivative of rate of change of sensor sensitivity, or a comparison of rate of change of sensor sensitivity to a priori rate of change sensitivity information.

18. The system of claim 15 wherein the sensor electronics configured to determine the likelihood of recovery based on the plurality of risk factors comprises evaluating a spectral content of the signal from the analyte sensor or noise patterns by at least one pattern recognition algorithm.

19. The system of claim 15, wherein the sensor electronics are configured to determine the end of life status by determining an end of life score based on the plurality of risk factors.

20. The system of claim 19, wherein the sensor electronics are configured to determine the end of life status based on the end of life score.

21. The system of claim 19, wherein the sensor electronics are configured to determine the end of life score by weighting one or more of the plurality of risk factors.

22. The system of claim 15, wherein each of the plurality of risk factors is partially indicative of the end of life of the analyte sensor based on a comparison of the risk factor to one or more criteria.

23. The system of claim 15, wherein the sensor electronics are configured to determine the end of life status by using a probability analysis.

24. The system of claim 15, wherein the output related to the end of life status is displayed on a user interface.

25. The system of claim 15, wherein the output related to the end of life status comprises instructions to change the analyte sensor.

26. The system of claim 15, wherein the output related to the end of life status comprises a data transmission.

27. The system of claim 15, wherein the sensor electronics comprise a processor, the processor comprising instructions stored in memory, wherein the instructions, when executed by the processor, cause the sensor electronics to perform the determining the likelihood of recovery, the determining the end of life status, or the providing the output.

28. The system of claim 15, wherein the sensor electronics are configured to provide the output by disabling display of sensor data.

* * * * *